US012751850B2

(12) United States Patent
Loke et al.

(10) Patent No.: US 12,751,850 B2
(45) Date of Patent: Oct. 6, 2026

(54) ADAPTIVE STIFFNESS ENERGY RETURN STRUCTURE FOR ORTHOPEDICS

(71) Applicant: Triton Systems, Inc., Chelmsford, MA (US)

(72) Inventors: Marmaduke J. Loke, Lowell, MA (US); George Santiago, Marlborough, MA (US); William M. Lindsey, Lowell, MA (US); Brian E. Moyer, Nashua, NH (US); Will Pieper, Chelmsford, MA (US)

(73) Assignee: Triton Systems, Inc., Chelmsford, MA (US)

( * ) Notice: Subject to any disclaimer, the term of this patent is extended or adjusted under 35 U.S.C. 154(b) by 0 days.

(21) Appl. No.: 19/037,900

(22) Filed: Jan. 27, 2025

(65) Prior Publication Data

US 2025/0241776 A1 Jul. 31, 2025

Related U.S. Application Data

(60) Provisional application No. 63/625,190, filed on Jan. 25, 2024.

(51) Int. Cl.
*A61F 5/01* (2006.01)

(52) U.S. Cl.
CPC ............ *A61F 5/0111* (2013.01); *A61F 5/012* (2013.01); *A61F 2005/0188* (2013.01); *A61F 2005/0197* (2013.01)

(58) Field of Classification Search
CPC .... A61F 5/0102; A61F 5/0104; A61F 5/0111; A61F 5/0113; A61F 5/0118; A61F 5/0127; A61F 5/013; A61F 2005/0188; A61F 2005/0197
USPC ........................................ 602/12, 23–30, 13
See application file for complete search history.

(56) References Cited

U.S. PATENT DOCUMENTS

| | | | | |
|---|---|---|---|---|
| 3,827,430 A * | 8/1974 | Fadden | ................. | A61F 5/0113 602/28 |
| 4,773,405 A * | 9/1988 | Reime | ................... | A61F 5/0106 602/25 |
| 6,010,474 A | 1/2000 | Wycoki | | |
| 7,462,160 B2 | 12/2008 | Nobbe et al. | | |

(Continued)

OTHER PUBLICATIONS

Eva Probsting et al, "Safety and walking ability of KAFO userswith the C-Brace® Orthotronic MobilitySystem, a new microprocessor stance andswing control orthosis", May 2016Prosthetics and Orthotics International 41(1).

(Continued)

*Primary Examiner* — Rachael E Bredefeld
*Assistant Examiner* — Seth R. Brown
(74) *Attorney, Agent, or Firm* — CALDWELL LLC

(57) ABSTRACT

An adaptive stiffness energy return structure for orthopedics, wherein the structure includes a first mount configured to engage with a user, a second mount configured to at least partially surround a portion of a body, and a strut assembly mechanically connected to the first mount. The strut assembly may include at least two strut layers, one or more displacing at least a strut layer of the at least two strut layers and effecting a gap between the at least two strut layers, wherein the one or more spacers comprises one or more of a static spacer configured to effect a constant gap distance and a dynamic spacer configured to vary the gap distance.

18 Claims, 14 Drawing Sheets

(56) References Cited

U.S. PATENT DOCUMENTS

| | | | | |
|---|---|---|---|---|
| 8,397,403 | B2 * | 3/2013 | Guenther .............. | A61F 5/0111 36/27 |
| 8,465,445 | B2 | 6/2013 | George | |
| 10,980,648 | B1 | 4/2021 | Lecomte et al. | |
| 2017/0296372 | A1 * | 10/2017 | Fay ........................ | A61F 5/0127 |
| 2020/0253773 | A1 * | 8/2020 | Logue ................... | A61F 5/0127 |
| 2022/0133519 | A1 | 5/2022 | Lerner et al. | |
| 2023/0277356 | A1 | 9/2023 | Loke et al. | |

OTHER PUBLICATIONS

Christopher S Crowe et al, Prosthetic and orthotic options for lower extremity amputation and reconstruction, Plast Aesthet Res 2019;6:4.

* cited by examiner

600

700

ADAPTIVE STIFFNESS ENERGY RETURN STRUCTURE FOR ORTHOPEDICS

CROSS-REFERENCE TO RELATED APPLICATIONS

This application claims the benefit of priority of U.S. Provisional Patent Application Ser. No. 63/625,190, filed on Jan. 25, 2024, and titled "ADAPTIVE STIFFNESS ENERGY RETURN STRUCTURE FOR ORTHOPEDICS," which is incorporated by reference herein in its entirety.

STATEMENT OF GOVERNMENT INTEREST

This invention was made with government support under contract/Job No. W81XWH-22-C-0102 awarded by DHA/USAMRDC/CDMRP. The government has certain rights in the invention.

FIELD OF THE INVENTION

The present invention generally relates to the field of orthopedics. In particular, the present invention is directed to an adaptive stiffness energy return structure for orthopedics.

BACKGROUND

Orthopedic devices are typically designed to withstand the highest energy demands to ensure durability over many cycles, often leading to a stiffer, less comfortable device for everyday activities. In order to accommodate both high- and low-demand situations, patients often need multiple devices. A device that is too stiff may be uncomfortable and inefficient for routine activities, whereas a device that is too flexible may not provide enough support during more intense activities. Additionally, as patients progress through rehabilitation, they may need adjustments in stiffness, often requiring new devices or costly modifications. Currently, device stiffness is generally determined during fabrication or through irreversible modifications or modular components that clinicians may adjust. However, these methods often compromise performance, either limiting high-energy activities for comfort or sacrificing comfort for higher energy demands.

SUMMARY OF THE DISCLOSURE

In an aspect, an adaptive stiffness energy return structure for orthopedics may include a first mount configured to engage with a first portion of a user's body, a second mount configured to mount to a second portion of the user's body, and a strut assembly mechanically connected to the first mount and the second mount. The strut assembly may include at least two strut layers, and one or more spacers displacing at least a strut layer of the at least two strut layers and effecting a gap between the at least two strut layers, wherein the one or more spacers comprise one or more of a static spacer configured to effect a constant gap distance and a dynamic spacer configure to vary the gap distance.

In another aspect, a method of using an adaptive stiffness energy return structure for orthopedics may include mounting a first mount to a first portion of a body, mounting a second mount to a second portion of the body, wherein a strut assembly mechanically connects the first mount and the second mount, and the strut assembly includes at least two strut layers, and one or more spacers displacing at least a strut layer of the at least two strut layers and effecting a gap between the at least two strut layers, wherein the one or more spacers include one or more of a static spacer configured to effect a constant gap distance and a dynamic spacer configured to selectively vary the gap distance.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1:
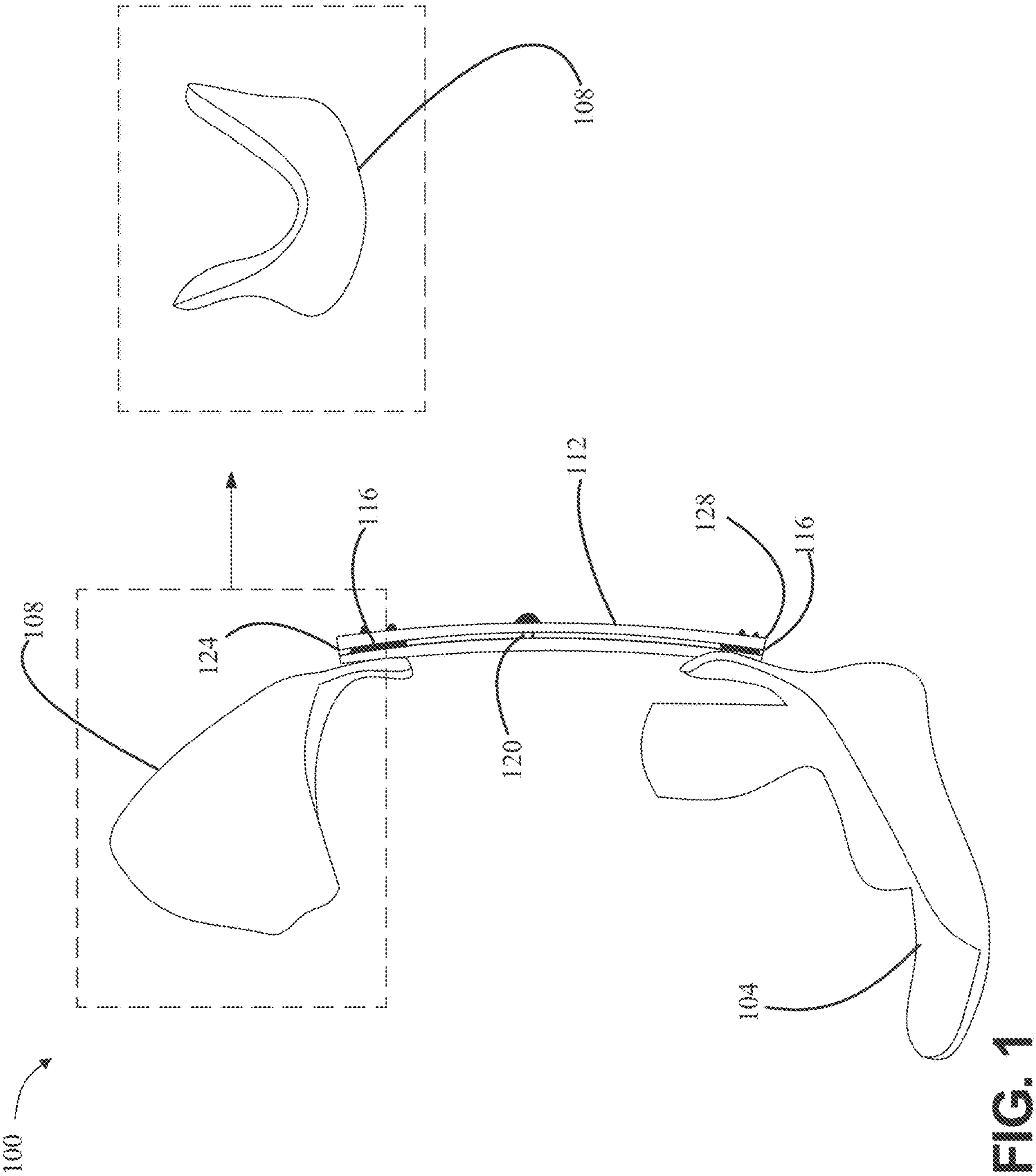
FIG. 1 is an exemplary embodiment of an adaptive stiffness energy return structure for orthopedics.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to structures for adaptive stiffness energy return structures for orthopedics. In an embodiment, the variable stiffness strut technology disclosed within allows for the response of an orthopedic device to varying load conditions to be continuously, selectively, and reversible changed. Current structures require an upfront decision about the stiffness of the device during fabrication and the choice requires compromising the performance of that device during some uses, either limiting the patient's high activity potential for better everyday use or creating a device which allows for high energy activity but limits non-jogging/running effectiveness. Current energy storing strut structures are either custom made to a particular stiffness or are prefabricated in a small number of discrete sizes and stiffnesses.

Aspects of the present disclosure can be used to provide a multi-use orthopedic device capable of adjusting its stiffness based on the user's interactions with the device or changes in external forces. Aspects of the present disclosure can also be used to modify current orthopedic devices. This is so, at least in part, because the structure as disclosed, allows for the strut assembly to be removed or added to orthopedic devices. The variable stiffness strut technology disclosed herein allows a patient to change the response characteristics of a single device based on their current need. Furthermore, this technology allows for much finer control over stiffnesses for a clinician than typical off-the-shelf strut structures.

Aspects of the present disclosure allow for an adaptive stiffness energy return structure for orthopedics. The orthopedic design described herein offers an innovative approach to the structural and therapeutic intervention and rehabilitation of lower limb musculoskeletal trauma, while delivering an adaptable, passive solution that enables recovery of primary neuromuscular function and strength, and an eventual return to duty. The present design does not suffer from key limitations present in competing treatment options. Exercise therapy regimens leveraging neuromuscular and proprioceptive activity alone have demonstrated efficacy but rely on underlying musculoskeletal structure for weight-bearing. Short-term benefits of early mobilization have won favor over immobilization by casting; however, pain and ankle joint instability often linger. The timing and magnitude of weight bearing, as variables that influence recovery, have largely been ignored when either treatment (mobilization or not) approach is considered. Traditionally fielded braces and wraps have effectively treated minor sprains but are not well suited to enable musculoskeletal recovery of more severe injuries. Powered exoskeletons and similar active technologies are bulky, heavy, expensive, and require complex adjustment to fit and adapt to each patient's body. Exemplary embodiments illustrating aspects of the present disclosure are described below in the context of several specific examples.

Referring now to FIG. 1, an exemplary embodiment of an adaptive stiffness energy return structure for orthopedics 100 is illustrated. In an embodiment, structure 100 may include a first mount 104 configured to engage with a user, a second mount 108 configured to a second portion of a body, and a strut assembly 112. Strut assembly 112 may include at least two strut layers, one or more spacers located between the at least two strut layers, and an actuator, wherein actuator is configured to adjust a spacing between the at least two strut layers.

In continued reference to FIG. 1, in an embodiment, structure 100 may include a first mount 104 configured to engage with a user. For purposes of this disclosure, a "mount" refers to a component or interface that secures or attaches structure 100 to a prosthetic limb, orthotic device, or body part. For example, and without limitation, first mount 104 may include a footplate. As used throughout this disclosure, a "footplate" is a, supportive surface or platform that is designed to engage with the foot in a structure. First mount 104 may assist structure 100 by distributing a user's weight evenly, providing stability during movement, and contributing to the alignment and motion of the lower limb. In some embodiments, first mount 104 may include shock-absorbing materials configured to reduce impact forces on the foot and lower limb when walking, running, or making other high-impact movements. Further, in some embodiments, first mount 104 may include features for stability and traction. For example, first mount 104 may include materials or design elements that are textured or treaded to provide traction and stability. In an embodiment, first mount 104 may include one or more features that support alignment of the foot and ankle in a particular orientation, supporting the correct biomechanics during movement. For instance, one or more features may ensure that a foot is positioned at the correct angle relative to the ground or that the user's center of gravity is balanced properly. This may include the use of one or more cushions or arch supports.

Still referring to FIG. 1, the manner in which first mount 104 engages with a user may vary depending on structure's 100 configuration. For example, first mount 104 may be configured to be in direct contact and/or indirect contact with the user, such as a user's foot. Direct contact may be illustrated in an embodiment wherein the first mount 104 comes into direct contact with a user's foot. In such an embodiment, first mount 104 may be molded or contoured to fit the specific shape of the foot, providing both comfort and functional support. In instances wherein indirect contact is made between a foot and first mount 104, the first mount 104 may interface indirectly with a foot through a liner or a sock. In one or more embodiments, first mount 104 may be adjustable and/or customizable. In some cases, first mount 104 may fit within a shoe, allowing a user to maintain consistency across their footwear. In one or more embodiments, first mount 104 may additionally include ankle support, wherein first mount 104 extends past a user's ankle.

In further reference to FIG. 1, in an embodiment, first mount 104 may include an arm plate, palm plate, hand plate, and/or a wrist plate. These embodiments may interface with a user's arm, palm, hand, and/or wrist providing for a distribution of forces during gripping, lifting, and/or other hand movements. These plates may play a similar role to a footplate, as discusses above, in that they may serve as the point of contact and energy transfer, absorbing forces and returning energy to assist with the movement of the arm. Depending on first mount's 104 design, it may also provide comfort, ensure proper alignment, and/or be tailored for individual needs, much like how a footplate is tailored for the foot in prosthetic or orthotic designs.

In continued reference to FIG. 1, in an embodiment, first mount 104 material may include a material that takes durability, comfort, flexibility, and breathability and hygiene into consideration. For example, first mount 104 material may include carbon fiber, thermoplastics, and/or composites for durability. In some embodiments, materials such as gel, foam, and/or soft cushioning layers may be integrated into first mount 104 for comfort. Further, in cases where flexibility is important, first mount 104 may include materials such as rubber, silicone, or specialized foams. Areas of first mount 104 that may be directly contacting a user's body may include material that is breathable and easily cleaned. For example, first mount 104 may include materials such as breathable textiles, antimicrobial fabrics, and/or moisturewicking layers. Further, in some embodiments of structure 100 wherein a pressure system is present, first mount 104 may include one or more pressure, torque and/or force sensors and one or more feedback mechanisms.

Still referring to FIG. 1, in an embodiment, first mount 104 may be mechanically connected to strut assembly 112. "Mechanically connected" refers to two or more components or parts that are physically joined or linked together in such a way that they transfer forces, motion, or energy between them. In an embodiment the mechanical connection may involve some form of physical attachment or coupling using mechanical means, such as fasteners, joints, or linkages. In some embodiments, the mechanical connection may be permanent (e.g., welding, riveting) and/or temporary (e.g., screws, bolts, clips). In one or more embodiments, the mechanical connection may be accomplished using a connecting assembly as described in greater detail below.

Continuing to reference FIG. 1, in an embodiment, structure 100 may include a second mount 108. For example, second mount 108 may include an offloading cuff configured to at least partially surround a limb of a body. In an embodiment, second mount 108 may be positioned at least partially around a user's knee. In some cases, second mount 108 may be positioned at least partially around a user's arm. Further in some cases, second mount 108 may be positioned at least partially around a user's neck. Second mount 108 may be configured to provide controlled compression and redistribution of forces. In an embodiment, second mount 108 may include a means for fastening, which may include one or more straps, cinches, and/or buckles. The means for fastening may enable a user to secure the second mount 108 to their body. In some embodiments, second mount 108 may be whole, in that a user may have to place their foot, arm, head, and/or the like, through one end and out the other end in order to wear structure 100. In such an embodiment, second mount 108 may still include a means for fastening to enable a user to securely fit second mount 108 to their body. In one or more embodiments, second mount 108 may be designed to fit snuggly against a user's body. This may include a configuration wherein there is a dip in the height of second mount 108 where a joint may sit.

Further referring to FIG. 1, in an embodiment, second mount 108 may include various materials for varying reasons. For example, second mount 108 may include neoprene, elasticated fabrics (e.g., spandex, Lycra, polyester blends), nylon or polyester, memory foam, gel or silicone inserts, medical-grade elastic bands (may include adjustable hook-and-loop fasteners), carbon fiber or composite reinforced materials, and/or breathable mesh fabrics.

Continuing to reference FIG. 1, second mount 108 may be mechanically connected to strut assembly 112. In one or more instances, this may include a connection by one or more connecting assemblies.

In further reference to FIG. 1, strut assembly 112 stiffness may depend on many factors including material choices, shape, density, and manufacturing methods. Various elements may be combined in multiple ways to create DS and CVS strut assemblies 112 including, among others, strength components, geometry components, connector components, and actuator components. Some elements may be a strength component, a geometry component, a connector component, or any combination. Strut assemblies 112 may be prefabricated for a number of stiffness ranges. Continuously variable stiffness (CVS) strut assembly 112 changes described herein may rely on manipulations of shape and or density to effect stiffness modification. When discrete stiffness (DS) and CVS strut elements are combined, the resulting strut assembly 112 may have a total stiffness that includes contributions from both elements. DS and CVS strut elements may be differentiated by how their stiffnesses may be changed or controlled: DS changes typically result and persist due to specific component choices made during orthopedic device assembly, whereas CVS struts may be manipulated post-assembly to effect stiffness. In an embodiment, a CVS strut element may be used to increase or reduce the stiffness of a strut assembly 112 through one or more manipulations. Because DS changes may result from choices made during orthopedic device assembly, they likely require a clinician and/or tools to effect change by adding, changing, or removing elements to/from a SA.

In continued reference to FIG. 1, CVS stiffness changes may result from a clinician's or an end-user's action (e.g., via mechanical interaction) or may occur via automated means (e.g., electro-mechanical actuation), such as in response to clinician/user commands (e.g., electronic button press) or in response to a detected performance requirement/activity demand. In one or more embodiments, strut assembly's 112 stiffness may be adjusted by a clinician or the patient. Who is able to make adjustments to strut assembly 112 stiffness may be reliant on the configuration of the structure 100. For example, certain embodiments may restrict a patient's ability to make stiffness modifications. As a further example, coarse adjustments via the spacer change method may be restricted to clinician adjustments only. This may be accomplished through the use of methods such as anti-tamper bolts. Alternatively, and/or additionally, fine adjustments via the forcing pin method may be made accessible to the patient and/or restricted to only clinician control.

Continuing to reference FIG. 1, in an embodiment, CVS technology may be incorporated into orthopedic devices during the fabrication process leading to a seamless integration of CVS. Further, in some embodiments, CVS technology may be incorporated into orthopedic devices comprising multiple prefabricated sub-components that are permanently joined together during assembly (e.g., a laminated orthopedic device constructed from prefabricated sub-components). A CVS strut assembly 112 may include one or more of these permanently attached sub-components. In some cases, CVS technology may be incorporated into orthopedic devices comprising multiple prefabricated sub-components that are joined together via reversible attachment means (e.g., an orthopedic device constructed by bolting together prefabricated sub-components). A CVS strut assembly 112 may include one or more of these reversibly attached sub-components.

In further reference to FIG. 1, in an embodiment, CVS technology may be incorporated into an existing orthopedic device or sub-component by attachment of a new sub-component with CVS capability (e.g., an existing strut assembly 112 may be modified to include CVS technology).

Still referring to FIG. 1, "stiffness," as used throughout this disclosure is the measure of the ability to resist deformation in the presence of a load. For example, a device with high stiffness requires a larger load to reach a level of deformation as compared to a device with a lower stiffness. A less stiff device may be more comfortable whereas a stiffer device tends to be better suited to activities that produce higher loads. In layman's terms, stiffness is best communicated by analogy to a spring. A spring is an element that deforms in response to a load. Generally, something that is "stiffer" requires more load to result in the same deformation. A spring is also considered an energy storage element in that energy of deformation can be returned as the element returns to its original configuration but, for non-ideal springs and for dampers, some energy may be dissipated. The amount of deformation resulting from a specific load may or may not be linear/directly proportional to the load and may or may not depend on the rate of load application. In summary, stiffness herein includes concepts of visco-elastic springs and dampers which, in terms of Orthopedics, relates to how a device responds to activity and is related to comfort.

In further reference to FIG. 1, a “strut” is an element that connects two components of an orthopedic device assembly and is used to transfer loads and/or energy from one location to another within that assembly. As used throughout this disclosure, a “strut assembly” is a strut created from elements which may include both discrete stiffness and continuously variable stiffness elements. In an embodiment, strut assembly 112 may be mechanically connected to first mount 104 and second mount 108. Further, strut assembly 112 may include at least two strut layers, one or more spacers located between the at least two strut layers, and an actuator, wherein actuator is configured to adjust a spacing between at least two strut layers. As used throughout this disclosure, a “strut layer” refers to a layer of material in a strut. In an embodiment, a strut layer may include one strut that has been split, totaling two strut layers. Alternatively, in an embodiment, at least two strut layers may include an individual strut, wherein strut assembly 112 includes at least two individual struts and each strut is one strut layer.

Still referring to FIG. 1, in an embodiment, each of the proximal 124 and distal 128 ends of at least two strut layers may be mechanically connected by one or more connecting assemblies. For purposes of this disclosure, a “connecting assembly” refers to a group of components or parts that are physically or mechanically linked together to function as a single unit or system. The parts in a connecting assembly may work together to perform a specific function, and the connections between them may be achieved through various methods, such as fasteners, joints, and/or other interlocking mechanisms. One or more connecting assemblies May include one or more bushings configured to reenforce one or more holes, one or more machine screws disposed within the bushings and the one or more holes, one or more washers, and one or more mounting plates attached opposite to the one or more bushings. In some embodiments, the one or mounting plates may include circular bosses that may protrude from the face of the plate. These circular bosses may house threads for bolt installation, while allowing for interaction of the members. The height of these standoffs may be easily adjusted.

In continued reference to FIG. 1, in an embodiment, strut assembly 112 may include at least two strut layers. At least two strut layers may include a modular family of composite struts that collectively offer variant levels of energy return, thereby supporting a range of activity levels and patient sizes. At least two strut layers may contribute to the stiffness of strut assembly 112 through both their material strength and geometric characteristics. At least two strut layers need not be uniform in cross section nor made from homogeneous material. In an embodiment, a single homogeneous strut layer of constant cross-sectional area may be the simplest type of Strut assembly 112. At least two strut layers may be combined (may or may not be adhered/continuously connected to each other), each with unique strength/geometric properties, to create unique stiffness strut assemblies 112. In an embodiment, changing at least two strut layers’ characteristics (e.g., adding/subtracting at least two strut layers, changing at least two strut layers’ material properties, and/or changing at least two strut layers’ geometries, among others), may lead to DS changes. In some embodiments, strut assembly 112 stiffness may be modified continuously (i.e., post-assembly) through manipulation of at least two strut layers’ geometry or material properties, which may lead to CVS changes.

Further referencing FIG. 1, in an embodiment, strut assembly 112 may include one or more spacers. One or more spacers and at least two strut layers may be differentiated by their intended effect on a strut assembly 112. While at least two strut layers may be intended to change both geometry and strut assembly 112 material strength characteristics, one or more spacers, although capable of changing material strength in a strut assembly 112, may be primarily intended to change stiffness through changes in the strut assembly 112 geometry. For purposes of this disclosure, “spacer” refers to a component, feature or part used to maintain, effect, or alter a distance within an assembly or structure, e.g., between two parts. In an embodiment, one or more spacers may include one or more static spacers 116 and/or one or more dynamic spacers 120. The location of one or more spacers may vary. For example, one or more spacers may be located between at least two strut layers. Alternatively, and/or additionally, one or more spacers may be positioned so that they surround strut assembly 112. For example, this may include an embodiment wherein one or more spacers include one or more rings that wrap around at least two strut layers and slide up and/or down effecting the space between at least two strut layers. In an embodiment, one or more spacers may act as a displacement system, wherein the displacement system displaces the at least two struts in a way that effects a change of the at least two struts, resulting in a change to resultant forces on the at least two struts when loaded. In an embodiment, the displacement of at least a strut layer of the at least two struts caused by the one or more spacers may vary a load on structure 100, such that the load is increased and/or decreased as a function of the gap distance between the at least two strut layers. Further, one or more spacers may not necessarily only effect gap distance, in some embodiments, one or more spacers may affect the geometric shape of strut assembly 112, causing changes in resultant forces applied to strut assembly 112.

In continued reference to FIG. 1, in an embodiment, a method by which one or more spacers may change stiffness is to set (and possibly maintain) a gap between at least two strut layers in strut assembly 112. One or more spacers need not be of uniform thickness, nor made from homogenous materials (e.g., a spacer could be ovalized, bulged, tapered, corrugated, or spongey, among many other possibilities). One or more spacers may be used to control both the minimum and maximum gap between at least two strut layers when adhered/attached to at least two strut layers (e.g., in the middle or creating a sandwich). Alternatively, and/or additionally, in some embodiments, when one or more spacers are merely placed (and not adhered/attached) between at least two strut layers, the configuration may maintain only a minimum gap. Although sometimes static, one or more spacers may be used to discretely affect stiffness, compressing or expanding one or more compliant spacers or manipulating one or more spacers post-assembly to change strut assembly 112 geometry which may lead to CVS changes. In an embodiment, one or more spacers may include one or more static spacers 116 and/or one or more dynamic spacers 120, wherein actuator is configured to adjust the one or more dynamic spacers 120 to set a gap between the at least two strut layers. As used here, “dynamic spacer” refers to a component, feature, or part in a structure that maintains a gap or distance between two parts, but unlike static spacers, it is designed to accommodate movement or changing conditions over time. For example, in structure 100 CVS changes to strut assembly 112 may embody the definition of dynamic spacer 120. In an embodiment, one or more dynamic spacers 120 may include a geometric system which may be configured to adjust the spacing of at least two strut layers. As used herein, a “geometric system” refers to a system of interconnected features, parts, or components that work together to achieve a specific displacement, transformation, motion, or function. In an embodiment, the geometric mechanism may be configured to adjust at least two strut layers as a function of one or more movements of a user. Alternatively, “static spacer,” as used throughout this disclosure, refers to an object or component used to maintain a fixed distance between two parts or surfaces in a structure. For example, structure 100 may include one or more static spacers 116 wherein the one or more static spacers 116 are discretely placed at both the proximal 124 and distal 128 ends of strut assembly 112 and sandwiched between at least two strut layers. In an embodiment, one or more spacers may include any combination of shims, wedges, CAMs, bladders, bushings, washers, etc.

In further reference to FIG. 1, in an embodiment, one or more spacers may include one or more shims. As used herein, “shims” are thin, often tapered pieces of material used to fill in spaces between objects (for support, leveling, or adjustment of fit). Herein, shims are spacers that add material to structure 100 to set and maintain and/or to continuously change gaps between at least two strut layers at discrete locations in a strut assembly 112 (versus a continuous Spacer) and/or to set/maintain space between a strut assembly 112 and other orthosis elements. In an embodiment, multiple shims may be included in a strut assembly 112. In such an embodiment, each shim may not be of uniform thickness nor made from homogenous materials when compared to other shims. In an embodiment, shims adhered/attached to at least two strut layers may limit both the minimum and maximum gap between those layers at the point of attachment while shims not adhered/attached to opposing strut layers may maintain only the minimum gap. Although in some embodiments, shims may be static, in other embodiments shims may be used to discretely affect stiffness by compressing or expanding a compliant shim (e.g., made from a softer viscoelastic material) or by manipulating a shim post-assembly to change strut assembly 112 geometry which may lead to CVS changes. In an embodiment, shims may include any shape effective for filling space between at least two strut layers. For example, shims may be flat, round, oval, wedge shaped, or specifically shaped to fit the space between at least two strut layers.

Continuing to reference FIG. 1, in an embodiment, one or more spacers may include a wedge. As used herein, a “wedge” is a simple mechanical device that consists of a triangular-shaped object or tool that tapers to a sharp edge or point. Wedges may be used to change the orientation of one orthosis element with respect to another (e.g., one strut layer with respect to another strut layer or one strut layer with respect to another orthosis device component) via non-parallel opposing surfaces. In an embodiment, a wedge may be used to modify an orthopedic device’s geometry (e.g., plantar/dorsiflex the foot with respect to the shank). Although static in some embodiments, wedges may also be used to discretely affect strut assembly 112 stiffness, compressing or expanding a compliant wedge or manipulating a wedge post-assembly to change strut assembly 112 geometry may lead to CVS changes. For example, a wedge element could modify CVS via forced translation between two other strut layers to increase/decrease the gap between those layers (like splitting a log). Two or more wedges may be placed together to maintain consistent part-to-part orientation while allowing gap changes through relative wedge translations.

In continued reference to FIG. 1, in an embodiment, one or more spacers may include a Cam. As used here, “cam” refers to a mechanical component that converts rotational motion into linear or reciprocating motion, or vice versa, through a precisely shaped surface. Cams may modify the gap between at least two strut layers by rotating and thus providing a mechanism for continuously varying strut assembly 112 stiffness. In an embodiment, cams may be embodied as solid elements rotating eccentrically. Further, in some embodiments, cams may be held in place by friction with other orthosis elements or with one or more fasteners. In some embodiments cams may push layers apart (setting the minimum gap) however, in other embodiments, cams may be designed to hold layers together (setting the maximum gap). In an embodiment a cam may include a threaded rod fashioned in such a way as to act as a cam. Such an embodiment may use actuator components, such as the threaded rod, and cam components in order to facilitate a bi-directional spacer.

In further reference to FIG. 1, in some embodiments, one or more spacers may include one or more bushings and/or washers. Bushings/washers may be placed on an axle or a threaded component to limit minimum and/or maximum separation between at least two strut layers. Although static, in some embodiments, bushings/washers may be used to discretely affect strut assembly 112 stiffness by compressing or expanding a compliant bushings/washer and/or manipulating a bushing/washer post-assembly to change strut assembly 112 geometry which may lead to CVS changes.

Further referencing FIG. 1, in an embodiment, one or more spacers may include a bladder. In some embodiments, a bladder is positioned between at least two strut layers of strut assembly 112. The bladder may be inflated using a pump and air to increase the distance between at least two strut layers. The bladder may be deflated to decrease the distance between one or more strut layers. Additionally, air is compressible, allowing the bladder to alter the geometry of strut assembly 112 and to directly alter the stiffness of the strut assembly 112 through the introduction of a compressible material. A bladder may be configured to inflate and/or deflate in response to external stimulus, thereby adjusting a gap between at least two strut layers. Bladders may be made from materials that can stretch, compress, and/or deform when subjected to changes in pressure, temperature, and/or other forces. In an embodiment, a bladder may be used to dynamically adjust a gap between prosthetic components, such as at least two strut layers, and/or between a body and a wearable device. In some embodiments, a bladder may include a hydraulic bladder, which may be used in structure 100 for controlled adjustments in pressure to alter a gap between two components, such as between at least two strut layers and/or between at least two strut layers and a part of a body. When pressure inside of the bladder is increased (by pumping fluid or air into it), the bladder may expand, pushing two components apart, thus creating a gap. Conversely, if the pressure is reduced, the bladder contracts, causing a gap to decrease. This may allow structure 100 to adapt to different energy loads by controlling the stiffness of strut assembly 112. Further, in some embodiments, the bladder may be utilized in a vibration isolation and dampening technique. Such an embodiment may use the bladder to dynamically adjust a gap between two structures that are subject to vibration or shock. A bladder may serve as a dynamic spacer or damping element in such a structure.

In continued reference to FIG. 1, in an embodiment, strut assembly 112 may include an actuator. As used throughout this disclosure, an "actuator" is a device that converts energy into mechanical motion, which is used to move or adjust the position of a component in a structure. Herein, an actuator may be responsible for moving and/or adjusting the spacing between at least two strut layers. Actuator may be used to change the stiffness of strut assembly 112 and include both manually and automatically controlled linear, rotary, electromagnetic, pneumatic, and/or hydraulic actuators, among others. In an embodiment, actuator may be used to manipulate stiffness at discrete times (i.e., periodically) and/or continuously. Actuator may affect material strength characteristics of strut assembly 112. Further, actuator may be used to modify orthopedic device stiffness through geometric manipulation of things like Cams, Wedges, Bushings, Washers, etc.

With continued reference to FIG. 1, an actuator may include a component of a machine that is responsible for moving and/or controlling a mechanism or system. An actuator may, in some cases, require a control signal and/or a source of energy or power. In some cases, a control signal may be relatively low energy. Exemplary control signal forms include electric potential or current, pneumatic pressure or flow, or hydraulic fluid pressure or flow, mechanical force/torque or velocity, or even human power. In some cases, an actuator may have an energy or power source other than control signal. This may include a main energy source, which may include for example electric power, hydraulic power, pneumatic power, mechanical power, and the like. In some cases, upon receiving a control signal, an actuator responds by converting source power into mechanical motion. In some cases, an actuator may be understood as a form of automation or automatic control.

With continued reference to FIG. 1, in some embodiments, actuator may include a hydraulic actuator. A hydraulic actuator may consist of a cylinder or fluid motor that uses hydraulic power to facilitate mechanical operation. Output of hydraulic actuator may include mechanical motion, such as without limitation linear, rotatory, or oscillatory motion. In some cases, hydraulic actuator may employ a liquid hydraulic fluid. As liquids, in some cases. are incompressible, a hydraulic actuator can exert large forces. Additionally, as force is equal to pressure multiplied by area, hydraulic actuators may act as force transformers with changes in area (e.g., cross sectional area of cylinder and/or piston). An exemplary hydraulic cylinder may consist of a hollow cylindrical tube within which a piston can slide. In some cases, a hydraulic cylinder may be considered single acting. Single acting may be used when fluid pressure is applied substantially to just one side of a piston. Consequently, a single acting piston can move in only one direction. In some cases, a spring may be used to give a single acting piston a return stroke. In some cases, a hydraulic cylinder may be double acting. Double acting may be used when pressure is applied substantially on each side of a piston; any difference in resultant force between the two sides of the piston causes the piston to move.

With continued reference to FIG. 1, in some embodiments, actuator may include a pneumatic actuator. In some cases, a pneumatic actuator may enable considerable forces to be produced from relatively small changes in gas pressure. In some cases, an pneumatic actuator may respond more quickly than other types of actuators, for example hydraulic actuators. A pneumatic actuator may use compressible flued (e.g., air). In some cases, a pneumatic actuator may operate on compressed air. Operation of hydraulic and/or pneumatic actuators may include control of one or more valves, circuits, fluid pumps, and/or fluid manifolds.

With continued reference to FIG. 1, in some cases, actuator may include an electric actuator. Electric actuator may include any of electromechanical actuators, linear motors, and the like. In some cases, actuator may include an electromechanical actuator. An electromechanical actuator may convert a rotational force of an electric rotary motor into a linear movement to generate a linear movement through a mechanism. Exemplary mechanisms, include rotational to translational motion transformers, such as without limitation a belt, a screw, a crank, a cam, a linkage, a scotch yoke, and the like. In some cases, control of an electromechanical actuator may include control of electric motor, for instance a control signal may control one or more electric motor parameters to control electromechanical actuator. Exemplary non-limitation electric motor parameters include rotational position, input torque, velocity, current, and potential. electric actuator may include a linear motor. Linear motors may differ from electromechanical actuators, as power from linear motors is output directly as translational motion, rather than output as rotational motion and converted to translational motion. In some cases, a linear motor may cause lower friction losses than other devices. Linear motors may be further specified into at least 3 different categories, including flat linear motor, U-channel linear motors and tubular linear motors. Linear motors may controlled be directly controlled by a control signal for controlling one or more linear motor parameters. Exemplary linear motor parameters include without limitation position, force, velocity, potential, and current.

With continued reference to FIG. 1, in some embodiments, an actuator may include a mechanical actuator. In some cases, a mechanical actuator may function to execute movement by converting one kind of motion, such as rotary motion, into another kind, such as linear motion. An exemplary mechanical actuator includes a rack and pinion. In some cases, a mechanical power source, such as a power take off may serve as power source for a mechanical actuator. Mechanical actuators may employ any number of mechanism, including for example without limitation gears, rails, pulleys, cables, linkages, and the like.

In further reference to FIG. 1, actuator may include a threaded rod component configured to adjust a distance between the at least two strut layers t, wherein rotating the threaded rod in a first direction causes the distance between the at least two strut layers to increase and rotating the threaded rod in a second direction causes the direction between the at least two strut layers to decrease. Further, in such an embodiment, the threaded rod may be capped with protective material in order to prevent damage to a contacted strut layer and to facilitate rotation. The protective material may include plastic, silicone, rubber, foam, and/or any other protective material that may be suitable for structure 100. In continuance of the discussion of such an embodiment, the one or more spacers may include at least a bushing, wherein the at least a bushing is disposed on the threaded rod and configured to modify a distance between at least two strut layers. The one or more spacers may further include a shim, wherein the shim is inserted at a discrete location and configured to modify a possible range of a gap between at least two strut layers. As used here, a "discrete location" refers to a specific, distinct position or place that is clearly defined and separate from other locations. For example, in structure 100, in discussion of the present embodiment, a shim may be located at both the proximal 124 and distal 128 ends of strut assembly 112 between at least two strut layers. In some embodiments, the shims may be fastened/adhered/connected to at least two strut layers. Further, in some embodiments, the shims may be sandwiched between at least two strut layers and a connecting assembly. In an embodiment, structure 100 may include a threaded rod including a grip, which may enable a user to easily rotate the threaded rod. A "grip," as disclosed herein, refers to the design of a surface of an object, wherein the design facilitates a secure hold. For example, a grip may include knobs, handles, dials, levers, and/or the like. In an embodiment, grips may be made of rubber, plastic, metal, silicone, and/or any other suitable material for structure 100. In some embodiments, the one or more grips may be affixed to the right-handed threaded and left-handed threaded rod. Lastly, in some embodiments, structure 100 may include a threaded rod including an anti-tamper bolt. An "anti-tamper bolt" is a type of fastener designed to prevent unauthorized or malicious removal, tampering, or manipulation. Such bolts are engineered to be difficult or impossible to remove without specialized tools or knowledge, making them useful in securing sensitive equipment, installations, or systems. For example, an anti-tamper bolt may include security bolts, shear bolts, tamper-evident bolts, one-way bolts, locking bolts, and/or the like.

Still referring to FIG. 1, in an embodiment, one or more actuators may include a right-handed threaded rod, threaded through a first hole, and a left-handed threaded rod, threaded through a second hole which opposes the first strut layer. This structure may be located near the center of strut assembly 112. In such an embodiment, the right-handed threaded rod may follow the standard threading convention, where turning it clockwise tightens the rod, and turning it counterclockwise loosens it. Whereas the left-handed threaded rod has the opposite threading convention; turning it clockwise loosens the rod, and turning it counterclockwise tightens it. By utilizing two rods with opposing threads, the movement of the rods will cause at least two strut layers or other components of strut assembly 112 to either move towards each other or move apart based on the direction of the rotation. For example, when the right-handed threaded rod is turned in a clockwise direction, it will tighten, pulling the components together, or causing at least two strut layers to compress towards each other. Simultaneously, the left-handed threaded rod, may be turned counterclockwise by the same motion of the actuator (or vice versa). This may cause the left-handed threaded rod to tighten, which may also pull the opposing components together. Conversely, when both rods are rotated in the opposite direction (counterclockwise for the right-handed threaded rod and clockwise for the left-handed threaded rod), both rods will loosen, and the components or at least two strut layers will move apart. In an embodiment, the net effect of using these two opposing threads is that the relative position between the two strut layers or components may be precisely adjusted by controlling the rotational direction and degree of movement of the rods. This may allow for compression or extension of strut assembly 112 in a linear direction and a tension adjustment within the structure, wherein the tension adjustment directly relates to the stiffness of the strut assembly 112.

In further reference to FIG. 1, in an embodiment, the right-handed threaded rod and the left-handed threaded rod may operate to adjust stiffness of structure 100 in different ways. For example, in an embodiment, the right-handed threaded rod may enable a user to make course adjustments, and the left-handed threaded rod may enable a user to make fine adjustments. "Course adjustments" refer to large, less precise changes to a structure or setting, often used to make broad alterations. Whereas "fine adjustments" refer to small, precise changes made to refine the structure, usually made after a course adjustment has been made.

Still referencing FIG. 1, in an embodiment, adjusting CVS struts may be actuated electronically (e.g., shape metal alloy inclusion, pneumatic bladder in/deflation, and/or linear/rotary actuators) via manipulation of a remote control, via an application on a mobile platform, or via other electronic input(s). In an embodiment, structure 100 may include an actuator with an electronic controller. In such an embodiment, the electronic controller may be configured to receive one or more electronic control signals and adjust the spacing between at least two strut layers as a function of one or more electronic control signals. For example, a user may use a remote to adjust the stiffness of at least two strut layers, wherein the remote sends one or more electronic signals to electronic controller at structure 100, and the electronic controller receives one or more electronic signals that function to move actuator configured to adjust at least two strut layers. In an embodiment, the electronic control signals may be sent to the controller from a user interface, sensors, or a higher-level system controller. The control signals may include various forms of data, such as manual input from a user (e.g., via a joystick, touchscreen, buttons, and/or the like), sensor feedback that continuously monitors parameters like position, force, temperature, or load, and/or external control systems. Wherein the external systems may be part of a larger network or system that communicates with the actuator to adjust the spacing based on other factors. For example, other factors may include system-wide environmental changes, load balancing, and/or the like. The signals may be analog or digital depending on the embodiment. The electronic controller may be responsible for interpreting the electronic control signals and using them to make decisions about how to adjust actuator. This process may include converting control signals into actionable commands, modulating actuator behavior, and adjusting for environmental factors. Converting control signals into actionable commands may include the controller interpreting input signals, calculating the required movement, and converting the required movement into a corresponding action for the actuator. For example, the electronic controller may receive an input signal from a remote controller indicating that the actuator should stiffen, and the actuator may act on at least two strut layers to move at least two strut layers apart. Modulating actuator behavior may include adjusting the amount of power supplied to actuator, causing it to extend, retract, or adjust at least two strut layers accordingly. Further the control may adjust the spacing in real-time based on changing conditions detected by sensors in the system. For example, if structure 100 is under a higher load, the controller may adjust the spacing to compensate for stress or strain.

Still referring to FIG. 1, in an embodiment, adjustments to strut assembly 112 stiffness may be made in response to sensed stiffness requirements/activity level through automated means. This may include active control of stiffness changing elements as well as passive changes to orthopedic device components. In an embodiment, structure 100 may further include a pressure sensor system, wherein the pressure system may be configured to detect a pressure datum and adjust the distance between at least two strut layers using the actuator in response to the sensed signal. Pressure sensor system may include a strain gauge and/or a load cell.

In some cases, a pressure sensor system may include a pneumatic pressure system, hydraulic pressure system, electromechanical actuators with pressure feedback, inflatable pressure systems, magnetorheological fluids and electromagnetic pressure systems, biomechanical pressure feedback systems, spring-loaded pressure systems with adjustable force levels, and/or the like. A "pressure datum" is a reference point or baseline pressure value that is sensed by a system, which is then used to influence or modify the structure's load support capabilities. In some cases, pressure data may include data related to mechanical quantities. As a non-limiting example, mechanical quantities may include force, torque, and/or the like. In one or more embodiments, the pressure sensor system may include a machine-learning model to predict a user's load capabilities and adjust the strut assembly 112 accordingly using actuator to adjust the spacing between at least two strut layers. A machine-learning model may be trained using exemplary patient specific physiological data, exemplary activity and movement data, exemplary environmental and contextual data, exemplary longitudinal data, exemplary data from similar patients, and exemplary sensor data and feedback correlated to exemplary adjustments to the distance between at least two strut layers. Patient-specific physiological data may include, without limitation, range of motion data, muscle strength, joint health/condition, bone density, tendon and ligament flexibility, pain levels, movement patterns, posture and alignment, and/or patient feedback. Further, activity and movement data may include data related to the type and intensity of activity a user is engaged in. For example, this may include an analysis of walking speed, gait analysis, motion capture or video analysis, activity levels, exercise or physical therapy engagement, and/or the like. Environmental and contextual data may include external factors that affect a user's needs for stiffness or flexibility. For example, this may include data related to environmental conditions, surface type, device type and function, and/or the like. Longitudinal data for adaptation and prediction may include data taken over a period of device use. For example, historical health data, device usage history, recovery or rehabilitation milestones, sensor-based feedback over time, and/or the like. Data from similar patients or population data may be used in the absence of sufficient individual data. For example, this may include data related to clinical guidelines, patient demographics, and/or similar cases. Once trained, the model may utilize real-time sensor data to adjust stiffness dynamically based on the user's needs. Further, context-aware data may be necessary to ensure structure 100's stiffness adjustments are appropriate for the current task or activity. For example, a user may need higher stiffness when climbing stairs but less stiffness when walking on level ground. The model may analyze the current task or posture and adjust accordingly. Further, in some instances, monitoring the user's fatigue level, which may be inferred from changes in movement patterns, muscle activity, or even hear rate, could influence stiffness adjustments in real time.

In continued reference to FIG. 1, in an embodiment, different methods of varying the stiffness of the strut assembly 112 to accommodate adaptation of the device may be used. This may include modifying the width of the struts, layer count of the composite, material changes and flexibilizers for the epoxy matrix, etc. Modifying the width of at least two strut layers may alter how much material is present in an individual strut, which can affect its bending stiffness and overall strength. For example, wider struts (with larger cross-sectional area) may be stiffer because they are able to resist bending more effectively under a load. Alternatively, narrower one or more struts (with a smaller cross-sectional area) may be more flexible, allowing for more deflection when subjected to the same load. Modifying the layer count of the composite may include increasing the layer count, which may increase the stiffness of an individual strut, as more layers provide more resistance to deformation and bending. Fibers in each layer may be oriented in a specific direction to maximize stiffness in certain axes. Whereas, decreasing the layer count may reduce the material's stiffness and make the strut more flexible. Modifying materials used to make one or more struts may impact the stiffness of each individual strut. For example, a higher-modulus material, such as carbon fiber, is stiffer and may carry more load with less deformation. Alternatively, a lower-modulus material, such as glass fibers and certain types of polymers, may be more flexible but may not bear as much load before deforming. As used here, a "flexiblizer" is an additive that can be introduced into the resin to increase flexibility. The "epoxy matrix" refers to the resin material that holds the reinforcing fibers, such as carbon fiber or fiber glass, together in a composite structure. By adding flexiblizers (plasticizers, rubbery additives, or other flexible compounds), the epoxy resin may become more ductile and less brittle. This may reduce the stiffness of the composite structure, making it more flexible. Conversely, without flexibilizers, the matrix may be more rigid, which may increase the stiffness of the overall composite.

With further reference to FIG. 1, in an embodiment, other potential methods for adjusting stiffness of strut assembly 112 may include modifying fiber orientation, modifying core materials, and/or modifying surface treatment or coatings. The direction in which fibers are aligned within the composite layers may affect stiffness. Aligning the fibers longitudinally (along the length of an individual strut) may result in greater stiffness in that direction, while cross-plying fibers may increase strength in multiple directions but may reduce stiffness. "Cross-plying" refers to the process of laying up multiple layers of material where each layer is oriented at different angles to one another. In some designs of strut assembly 112, at least two strut layers may utilize honeycomb cores or foam cores within an individual strut to provide stiffness with minimal weight. These cores may be made of lightweight materials like foam or honeycomb structures that increase the bending stiffness without adding significant mass. Further, the surface properties of the composite, such as coatings for corrosion resistance or friction control, may play a role in the perceived stiffness in certain conditions.

In continued reference to FIG. 1, in an embodiment, strut assembly 112 may include a Turnbuckle. A Turnbuckle is a counter threaded rod placed between an anterior and posterior strut member allowing for adjustment of the device stiffness. Rotating the rod forces the centers of the strut members apart increasing the modulus of the assembly.

Still referring to FIG. 1, in an embodiment, strut assembly 112 may include a Spacer Strut. A spacer strut is an embodiment wherein a spacer material is placed between two strut members to coarsely adjust the stiffness of the assembly.

Continuing to reference FIG. 1, in an embodiment, strut assembly 112 may include a layered strut assembly 112, which may otherwise be referred to as a leaf spring strut assembly 112 and/or a laminar strut assembly 112. In such an embodiment, the strut members are made out of stacks of thin prefabricated strut layers. This gives a clinician fine control over the strength, weight and stiffness of the strut.

In further reference to FIG. 1, in an embodiment, strut assembly 112 may include a Laminar strut assembly 112. Such an embodiment may be created by stacking thin, prefabricated strut layers together and attaching them to other elements to create an orthopedic device. The strut layers in a Laminar strut assembly 112 may be attached by fastening, gluing, wrapping with carbon fiber or fiberglass, and/or a combination of any of the above. In this embodiment, strut layers may be different from each other in terms of cross-sectional area along their length and/or material strength. strut layers may also be of non-uniform geometric and/or strength characteristics (e.g., thin at one or more ends and thicker/thinner at other points along their length). Strut layers may also be made such that opposing surfaces could be anti-parallel and/or non-planar (e.g., one surface might be flat while the opposite surface could be rounded or dramatically thicker at specific points). A Laminar strut assembly 112 may provide clinicians with fine control over an orthopedic device's initial discrete stiffness and weight. Further, in some embodiments, Laminar strut assemblies 112 may include gaps between at least two strut layers which may be set using one or more spacers as previously described. In some embodiments, one or more shims may be inserted at discrete locations between strut layers and/or between strut assembly 112 and other elements of an orthosis to change structure 100's stiffness. In an embodiment, Laminar strut assemblies 112 may include CVS capability if one or more integrated strut layers contain CVS technology and/or if mechanisms for changing shim/spacer geometry post-initial assembly have been included/added.

In continued reference to FIG. 1, in some embodiments, strut assembly 112 may include a Spreading strut assembly 112. In such an embodiment, structure 100 may permit strut assembly 112 stiffness changes by changing the geometric relationships among at least two strut layers by spreading them further apart to increase stiffness. In this specific embodiment, rotation of a Cam (e.g., a rotating threaded rod) in one direction causes the gap between two strut layers to increase, resulting in increased stiffness. Cam rotation in the opposite direction permits the strut assemblies 112 to return to its undeformed configuration and stiffness. In a simple embodiment of a Spreading strut assembly 112, one end of a threaded rod (with only one thread direction) is attached via a threaded insert through a hole in one strut layer and therefore pushes against the opposite strut layer or another orthosis device element when rotated in one direction. In such an embodiment, the end of the threaded rod directly contacting the opposing strut layer may be capped with protective material to prevent damage to the contacted Strut Layer and/or to facilitate rotation (e.g., via a swivel joint end cap).

In further reference to FIG. 1, in an embodiment, the nominal stiffness of a Spreading strut assembly 112 that uses a Cam or threaded rod to push on a strut layer may be changed through placement of a Shim between the end of the Cam or threaded rod and the strut layer that it contacts. In some embodiments, the nominal stiffness a Spreading strut assembly 112 with threaded rods may also be modified by inclusion of a bushing(s) on the threaded rod between two strut layers to limit the minimum gap between the two strut layers. In an embodiment, wherein a Spreading strut assembly 112 utilizes one or more threaded rods, the length of the threaded portion of the rod, which may be limited via a bushing, limits the maximum gap between that can be set between two opposing strut layers. In one or more embodiments, a knob may be placed on a Cam or threaded rod for some embodiments of a Spreading strut assembly 112 to facilitate ease of CVS adjustment. Further, in some embodiments, a tool may be required to rotate a Cam/threaded rod of a Spreading strut assembly 112. For example, in an embodiment, a Spreading strut assembly 112 may be locked through inclusion of a keyway or set screw to prevent unintentional rotation of the rod.

Continuing to reference FIG. 1, in an embodiment a Spreading strut assembly 112 that may utilize both right- and left-hand threaded ends of a threaded rod, each of which may be threaded through corresponding holes in opposing strut layers. Such an embodiment may include a bolt-on Spreading strut assembly 112 which may include one or more shims between strut layers at both the proximal 124 and distal 128 ends. Further, such an embodiment may include a knob pinned to a right- and left-hand threaded rod, which may facilitate rotation of the threaded rod in one direction resulting in thrust resisted by corresponding threaded inserts which spreads strut layers further apart. Rotating the knob/threaded rod in the opposite direction permits strut layers to return to an undeformed (unspread or less spread) arrangement. Further, such an embodiment may include reinforced through-holes machine screws, washers, and mounting plates that may be laminated in proximal and distal orthosis member layups.

In further reference to FIG. 1, in an embodiment, strut assembly 112 may include a Spreading/Gathering strut assembly 112. For example, the utility of pushing strut layers apart to increase stiffness for Spreading strut assembly 112 may be extended to include actuation to pull strut layers closer together to decrease stiffness. One embodiment of a Spreading/Gathering strut assembly 112 may utilize a threaded rod with both right- and left-hand threaded ends, each of which is threaded through corresponding holes in opposing Strut Layers. In such an embodiment, the threaded holes may be capable of accepting bi-directional (push and pull) thrust such that, as the threaded rod is rotated in one direction the gap between opposing strut layers is increased to increase the stiffness of the strut assembly 112 and, when the threaded rod is rotated in the opposite direction, the gap is decreased to reduce the stiffness of the strut assembly 112.

In continued reference to FIG. 1, in an embodiment a Spreading/Gathering strut assembly 112 may be realized through various other mechanical linkages. For example, in some embodiments, a strap(s) may be connected to the distal 128 end and the proximal 124 end of a strut assembly 112. The strap may be configured to pull the distal 128 end and the proximal 124 end closer together to alter the stiffness of the SA. Further, the straps may be configured to increase the distance between the distal 128 end and the proximal 124 end to alter the stiffness of the strut assembly 112. In some embodiments, a linear actuator is configured to control the strap and to thus control the distance between the distal 128 end and the proximal 124 end. A linear actuator may comprise a handle and be configured to increase the stiffness of the SA when the handle is activated by a user. The linear actuator may further be configured to decrease the stiffness of the strut assembly 112 when the handle is released.

Still referring to FIG. 1, in some embodiments, structure 100 may include a computing device. Computing device includes a processor communicatively connected to a memory. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, Computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device may include a single computing device operating independently, or may include two or more computing device operating in concert, in parallel, sequentially or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device may include but is not limited to, for example, a computing device or cluster of computing devices in a first location and a second computing device or cluster of computing devices in a second location. Computing device may include one or more computing devices dedicated to data storage, security, distribution of traffic for load balancing, and the like. Computing device may distribute one or more computing tasks as described below across a plurality of computing devices of computing device, which May operate in parallel, in series, redundantly, or in any other manner used for distribution of tasks or memory between computing devices. Computing device may be implemented, as a non-limiting example, using a "shared nothing" architecture.

With continued reference to FIG. 1, computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Figure 2:
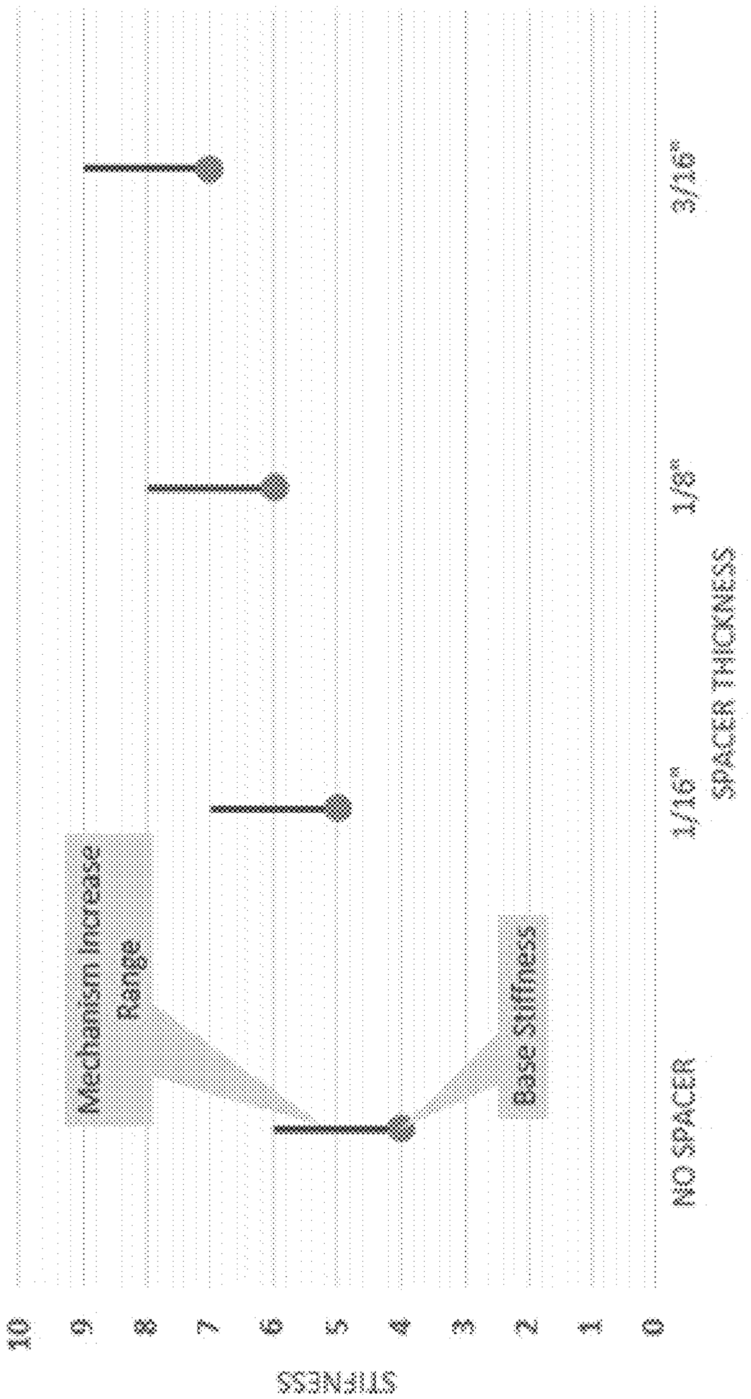
FIG. 2 is a chart illustrating combined discrete stiffness and continuously variable stiffness for a spreading strut assembly embodiment with four different fixed shim thicknesses.

Now referring to FIG. 2, illustrated is a chart depicting combined DS and continuously variable stiffness for a spreading strut assembly embodiment with four different fixed shim thicknesses. Further, it depicts the potential stiffness of an embodiment having a Spreading strut assembly, across four levels of DS as determined by spacer thickness assuming that the increased stiffness range provided by the CVS mechanism remains comparable for all four arrangements. Specifically, this is based on the embodiment as illustrated in FIG. 4.

Figure 3:
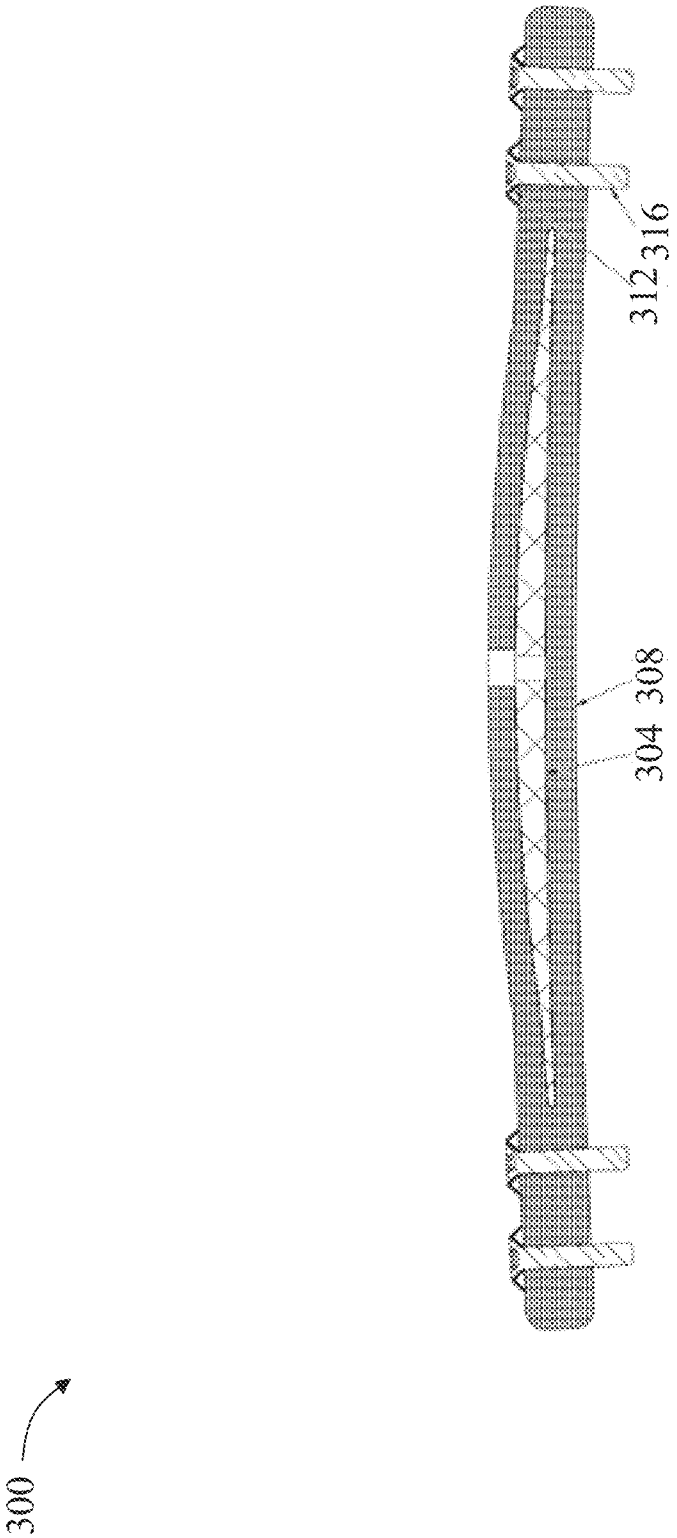
FIG. 3 is an exemplary embodiment of a prefabricated, non-uniform thickness spacer strut assembly for inclusion with an orthosis via layup integration.

Now referring to FIG. 3, illustrated is an exemplary embodiment of a prefabricated, non-uniform thickness spacer strut assembly 300 for inclusion with an orthosis via layup integration. In such an embodiment, a non-uniform spacer 304 may be used to adjust the space between a split strut 308. Strut assembly 300 may be attached to a footplate and/or an offloading cuff with washers 312 and machine screws 316 and/or a bolt assembly. Such an embodiment, such as strut assembly 300 may create a DS strut assembly that may be included in a custom layup. As used throughout this disclosure, "orthosis" is a medical device or support that is used to align, support, or correct the function of a limb. A "layup," as used herein, refers to a technique where layers of material are laid down or stacked in a specific pattern or orientation to create a durable and structured form. The layers of such material may include, but are not limited to fiberglass, carbon fiber, and/or composite materials.

Figure 4:
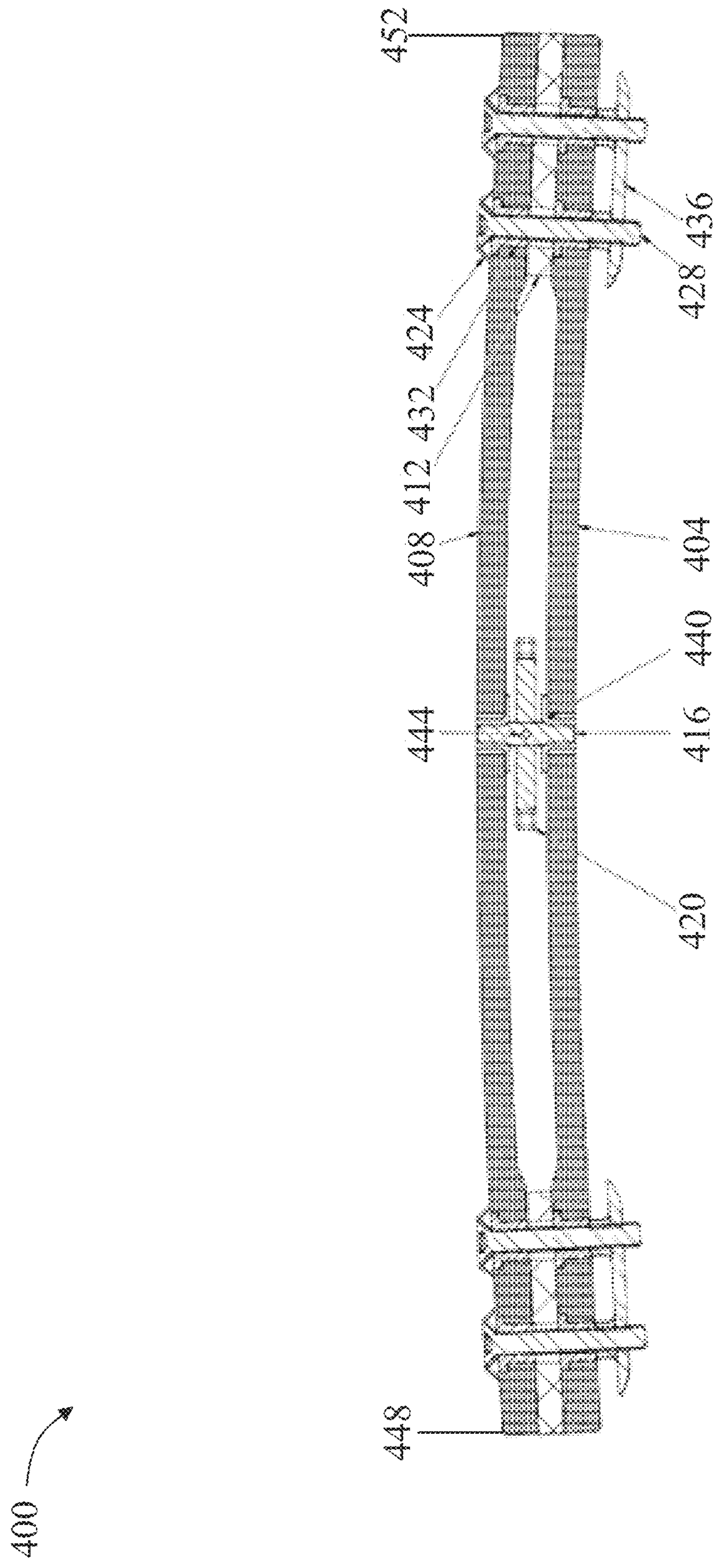
FIG. 4 is an exemplary embodiment of a bolt-on spreading strut assembly.

Now referring to FIG. 4, illustrated is an exemplary embodiment of a bolt-on spreading strut assembly 400. In an embodiment, strut assembly 400 may include square shims 412 located between strut layers 404 and 408 at both the proximal 448 and distal 452 ends of strut assembly 400. Further, strut assembly 400 may include a knob 420 that is pinned, using a pin 444, to a right- and left-hand threaded rod 416 and is intended to spread at least two strut layers apart via rotation in one direction resulting in thrust resisted by corresponding threaded inserts 440. In an embodiment, rotating the knob 420 in the opposite direction may permit the at least two strut layers to return to their undeformed arrangement. Bushing reinforced through-holes 432, machine screws 428, washers 424, and mounting plate 436 may be laminated into proximal and distal orthosis member layups.

Figure 5:
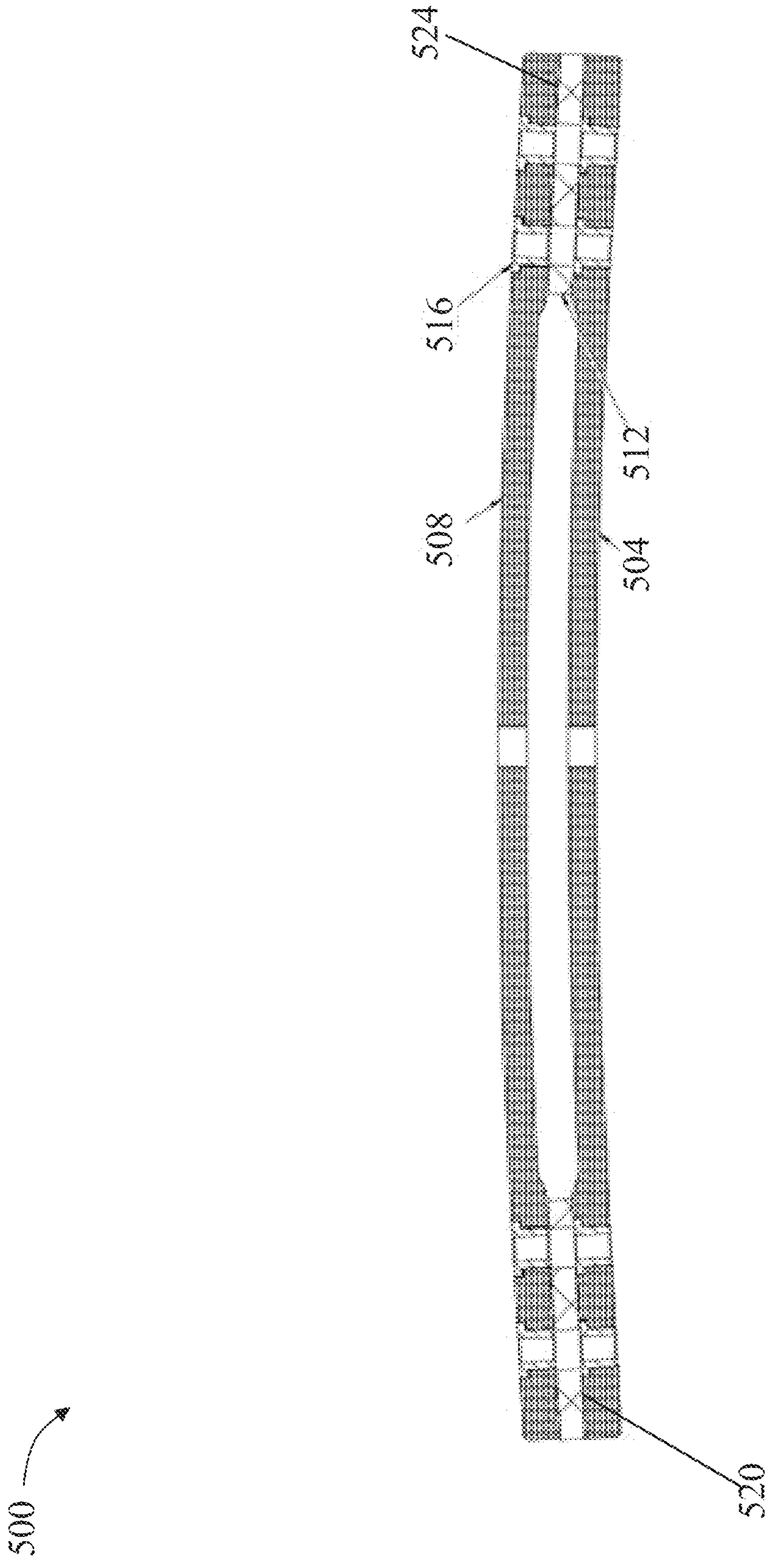
FIG. 5 is an exemplary embodiment of a bolt-on discrete stiffness strut assembly with two strut layers and two uniform thickness shim components.

Now referring to FIG. 5, illustrated is an exemplary embodiment of a bolt-on discrete stiffness strut assembly 500 with two strut layers and two uniform thickness shim components. The anterior strut 504 and posterior strut 508 may enclose one or more square shims 512 that may be attached at both the proximal 520 and distal 524 attachment points of strut assembly 500. The attachment points may be reinforced by one or more bushing hole reinforcements 516.

Figure 6:
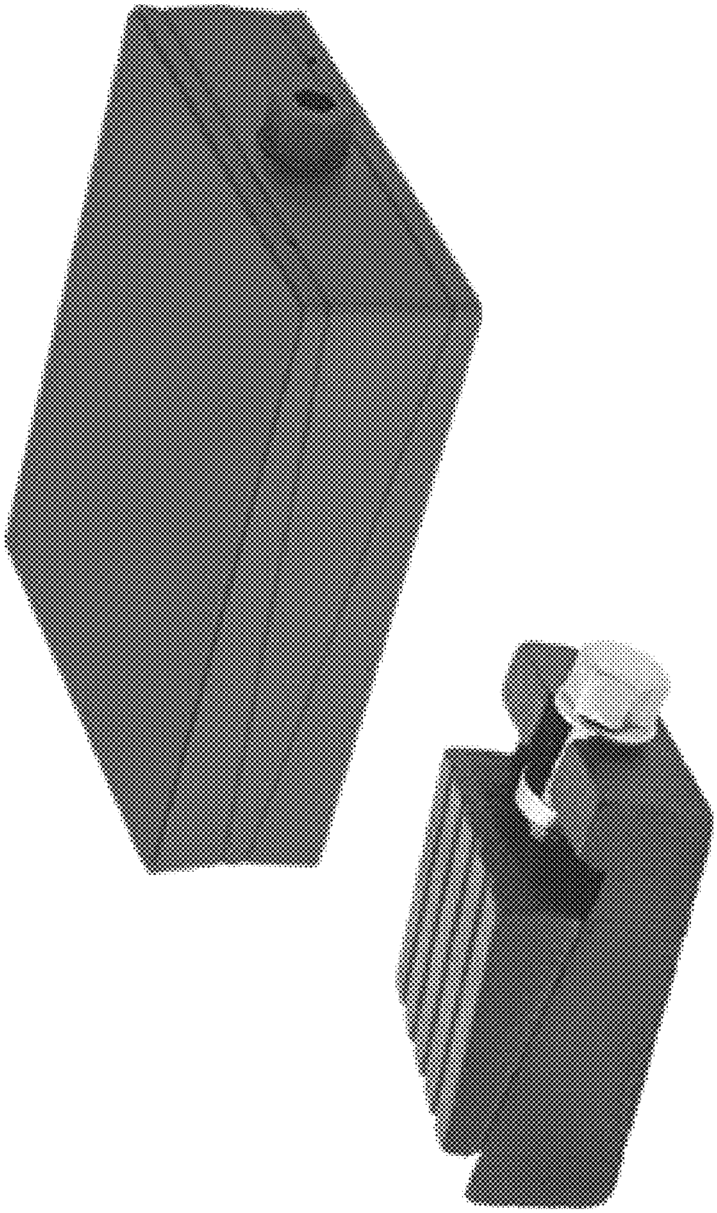
FIG. 6 illustrates exemplary wedge devices that may be utilized in a continuously variable stiffness strut assembly.

Now referring to FIG. 6, illustrated are exemplary wedge devices 600 that may be utilized in a continuously variable stiffness strut assembly. Alternatively, in some embodiments, wedge device 600 may be used to introduce CVS features to a strut assembly. In some cases, wedge devices 600 may include actuated wedges that may be used to mechanically spread two parallel surfaces apart, including at least two strut layers.

Figure 7:
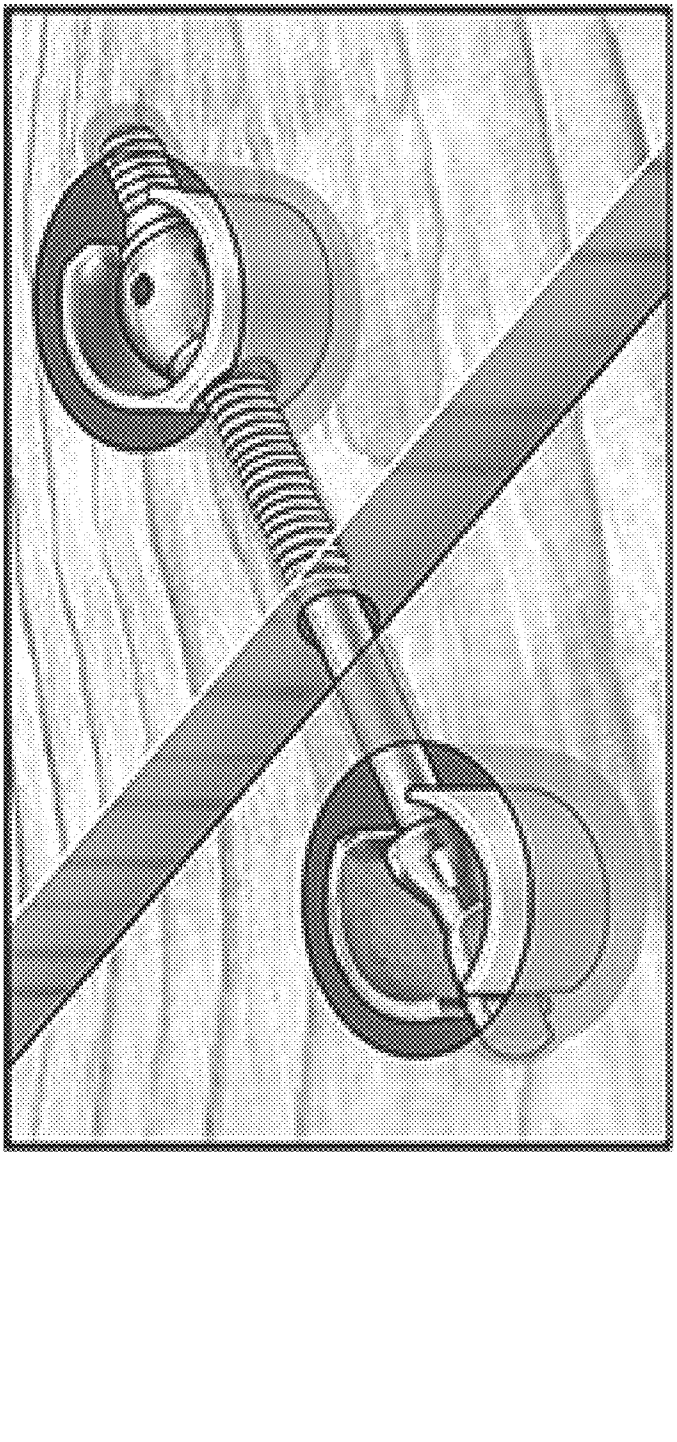
FIG. 7 is an exemplary embodiment of a mechanism that may be utilized to produce a spreading or gathering continuously variable stiffness strut assembly.

Now referring to FIG. 7, illustrated is an exemplary embodiment of a mechanism 700 that may be utilized to produce a spreading or gathering continuously variable stiffness strut assembly. In an embodiment, mechanism 700 may be used to either pull two surfaces together or push two surfaces apart via a threaded rod with only one thread direction. The wooden element in this figure represents strut layers for the use case described herein but does not necessarily limit at least two strut layers to such a material.

Figure 8:
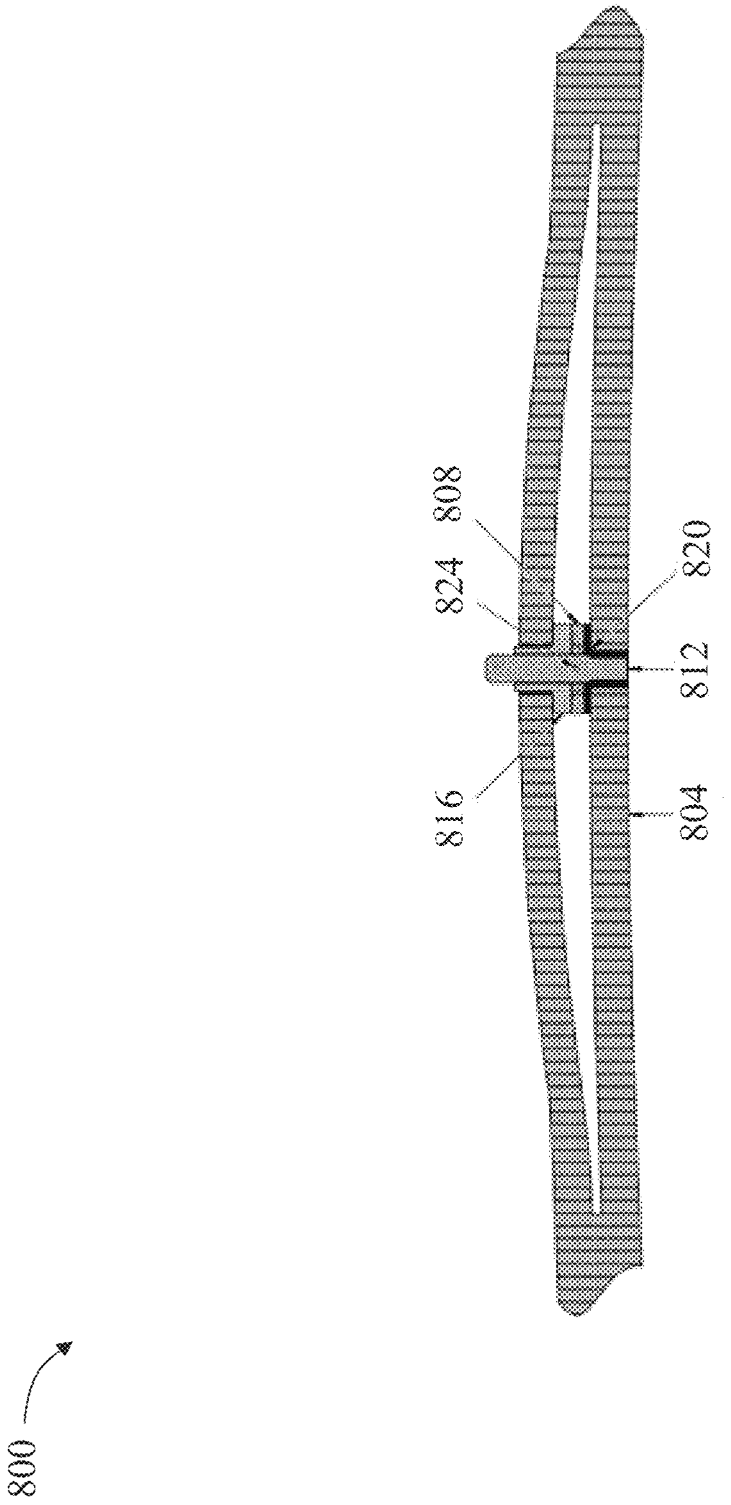
FIG. 8 is an exemplary embodiment of at least two strut layers, wherein a round shim and a bushing are configured to limit the minimum gap between the at least two strut layers.

Now referring to FIG. 8, illustrated is an exemplary embodiment of a strut assembly 800 having at least two strut layers, wherein a round shim 808 and a flanged sleeve bushing 816 are configured to limit the minimum gap between the at least two strut layers. Strut assembly 800 may include a spreading strut assembly with a round shim 808, a threaded rod 812, bushing 816, threaded inserts 820, and a pin 824. In an embodiment, strut assembly 800 may include a CVS strut assembly and may include strut layers, including a split strut 804, that has been laminated together. This may illustrate an exemplary prefabricated unit that may be attached to other orthosis elements either mechanically or via lamination.

Figure 9:
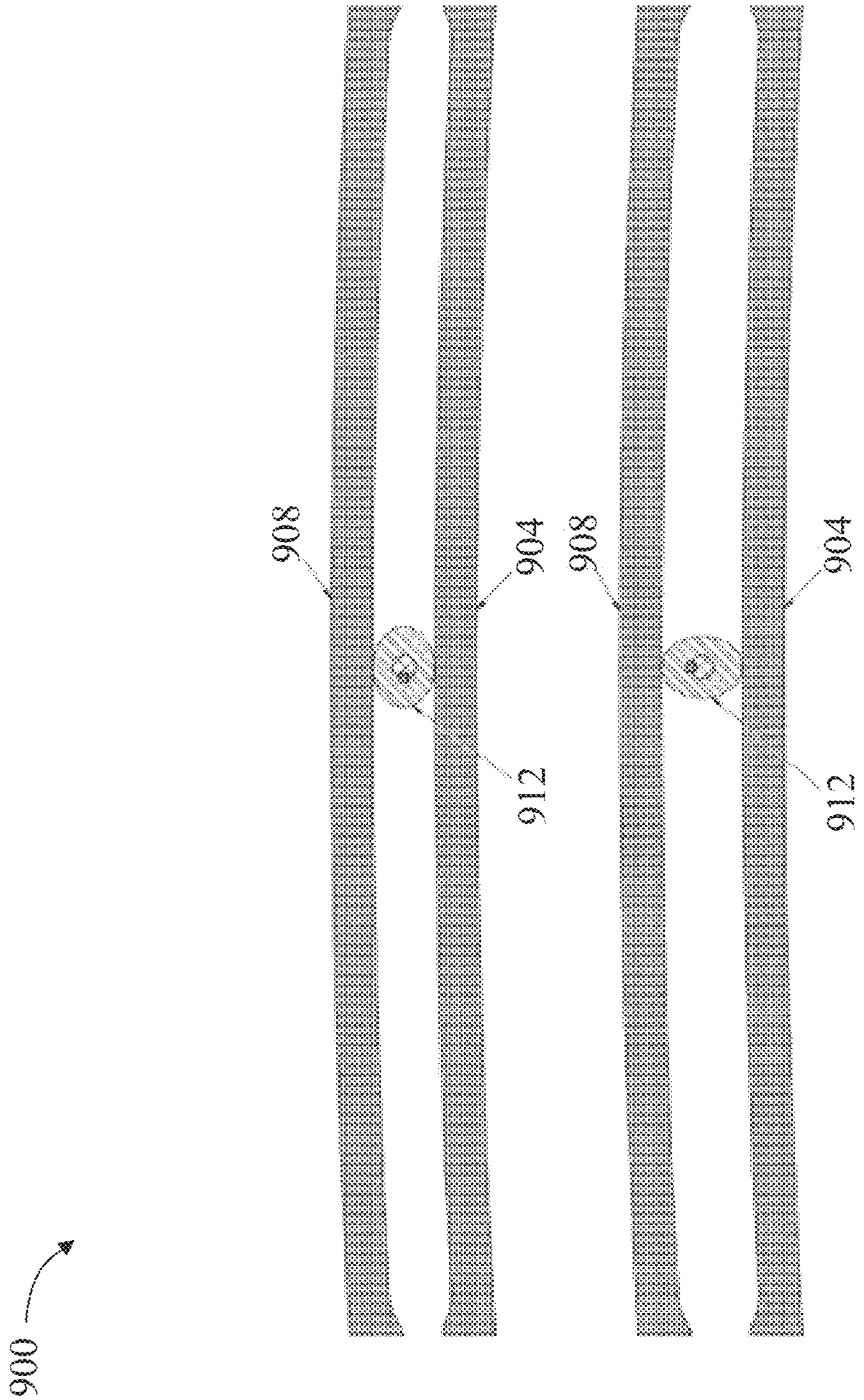
FIG. 9 is a schematic illustration of a CAM spreader embodiment.

Now referring to FIG. 9, illustrated is a schematic illustration of a CAM spreader embodiment 900. In an embodiment CAM spreader embodiment 900 is a strut assembly that may include two independent strut layers and a CAM spacer 912. Each of the independent strut layers may include an anterior strut 904 and posterior strut 908. The CAM spreader embodiment 900 may be configured to switch between two different geometries, and thus two different stiffness levels, via rotation. Each of these three components may be laminated together to create a CVS strut assembly unity or alternatively, the components may be mechanically connected to other orthopedic device elements to allow future modification of the nominal stiffness and/or CVS stiffens. In an embodiment, in an embodiment wherein the components are mechanically connected it may permit changes to the CVS actuation geometry or mechanism.

Figure 10:
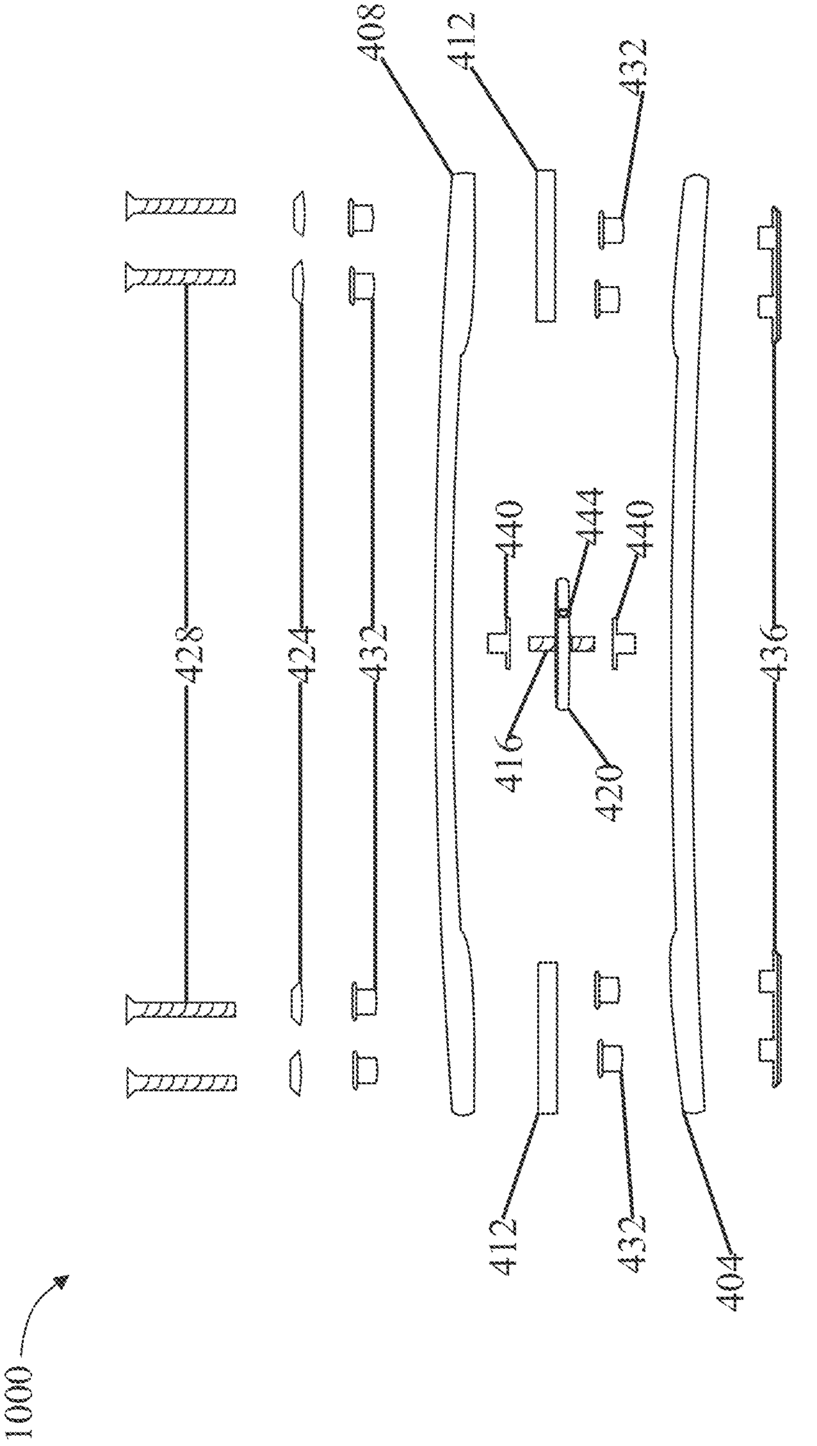
FIG. 10 is an exploded view of an embodiment of the device illustrated in FIG. 4.

Now referring to FIG. 10, illustrated is an exploded view 1000 of device 400 illustrated in FIG. 4. In an embodiment, view 1000 illustrates components of device 400, including: anterior strut 404, posterior strut 408, square shims 412, RH/LH threaded rod 416, knob 420, washers 424 machine screws 428, bushing hole reinforcement 432, mounting plates 436, threaded inserts 440, and a pin 444.

Figure 11:
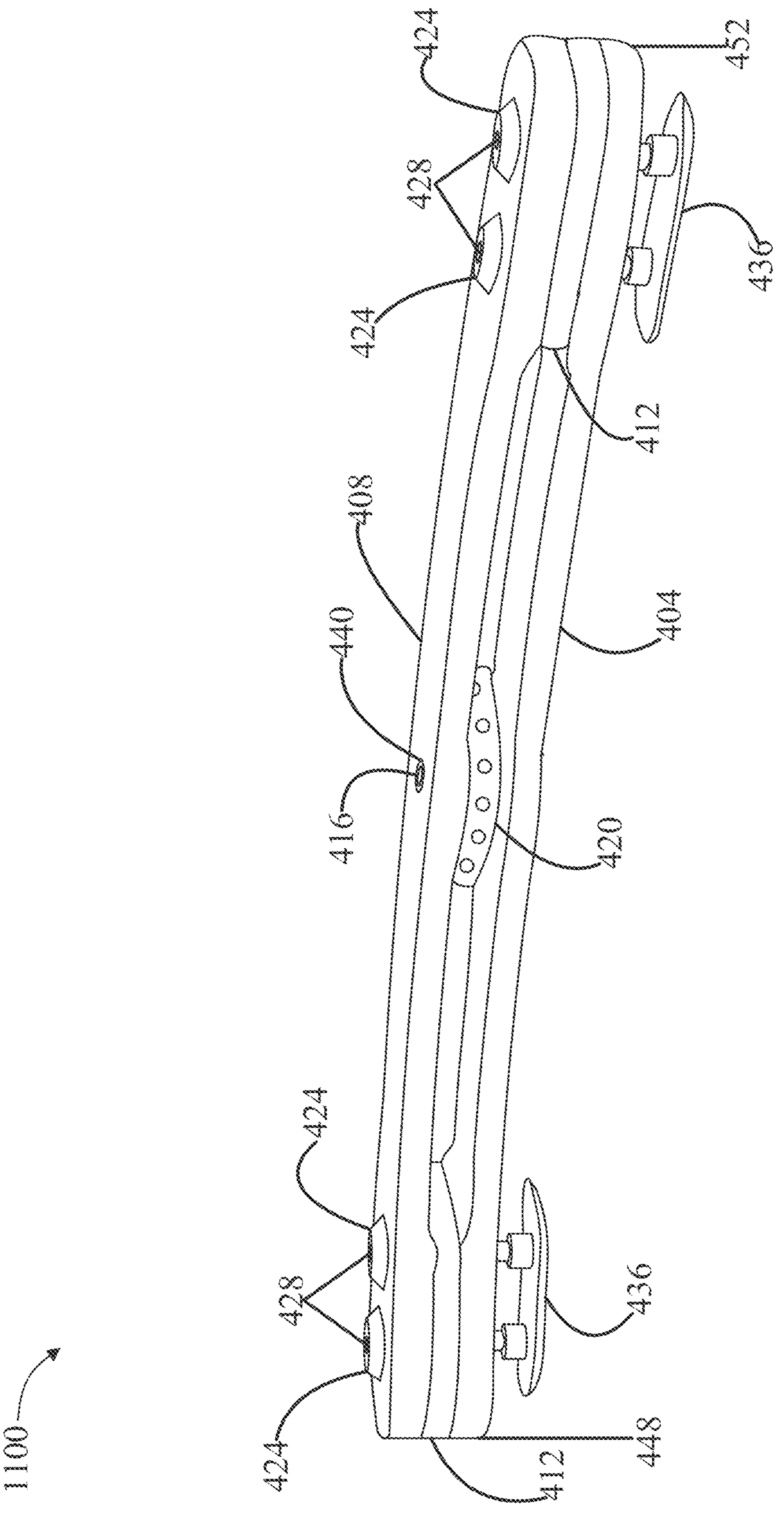
FIG. 11 illustrates a view of an embodiment of the device illustrated in FIG. 4.

Now referring to FIG. 11, illustrated is a view 1100 of the device 400 illustrated in FIG. 4. In an embodiment, strut assembly 400 may include square shims 412 located between anterior strut 404 and posterior strut 408 at both the proximal 448 and distal 452 ends of strut assembly 400. Further, strut assembly 400 may include a knob 420 that is pinned, using a pin, to a right- and left-hand threaded rod 416 and is intended to spread at least two strut layers apart via rotation in one direction resulting in thrust resisted by corresponding threaded inserts 440. In an embodiment, rotating the knob 420 in the opposite direction may permit the at least two strut layers to return to their undeformed arrangement. Bushing reinforced through-holes, machine screws 428, washers 424, and mounting plate 436 may be laminated into proximal and distal orthosis member layups. Not seen in this illustration is the pin and the bushing reinforced through-holes as the view does not allow for it.

Figure 12:
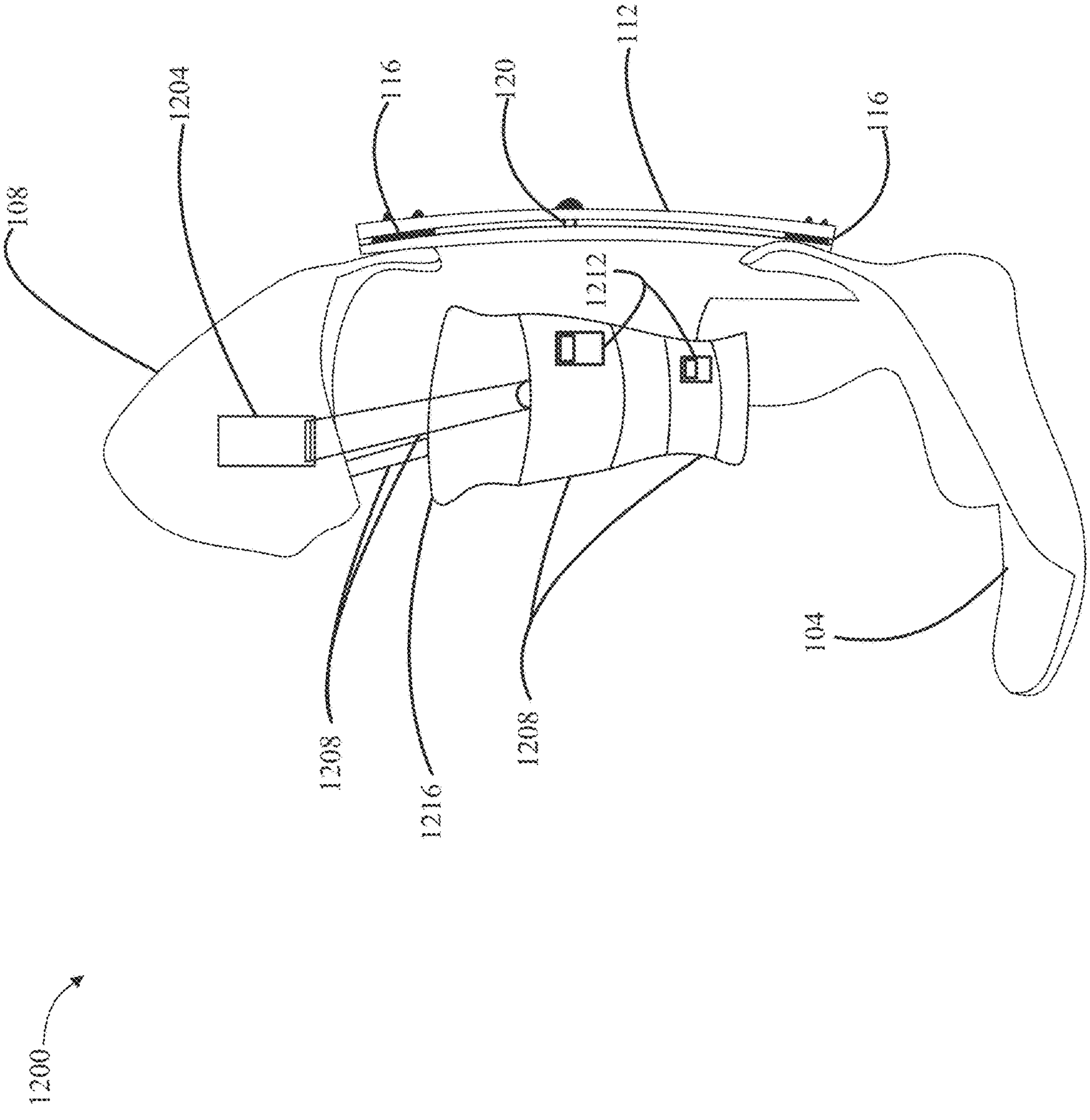
FIG. 12 illustrates an exemplary embodiment of an adaptive stiffness energy return structure.

Now referring to FIG. 12, illustrated is an exemplary embodiment of an adaptive stiffness energy return structure 1200 including one or more straps. In an embodiment, a strut assembly may include a first mount 104, and a strut assembly. The strut assembly may include both static spacers 116 and dynamic spacers 120. Further, in an embodiment, structure 1200 may include an actuator 1204, one or more straps 1208, one or more buckles 1212, and an ankle cuff 1216. An "ankle cuff" refers to a band or clasping means that wraps around the ankle and is configured to secure structure 1200 to a user's ankle. The one or more straps 1208 may be configured to adjust to a user's needs. This may include adjustments for comfort as well as adjustments for stiffness needs. Structure 1200 may be included in any previous embodiment discussed in relation to strut assembly 116. The ankle cuff 1216 and one or more straps 1208 may add additional CVS elements to overall structure of structure 1200. In one or more embodiments, actuator 1204 may assist in adjusting the one or more straps attached to ankle cuff 1216.

Figure 13:
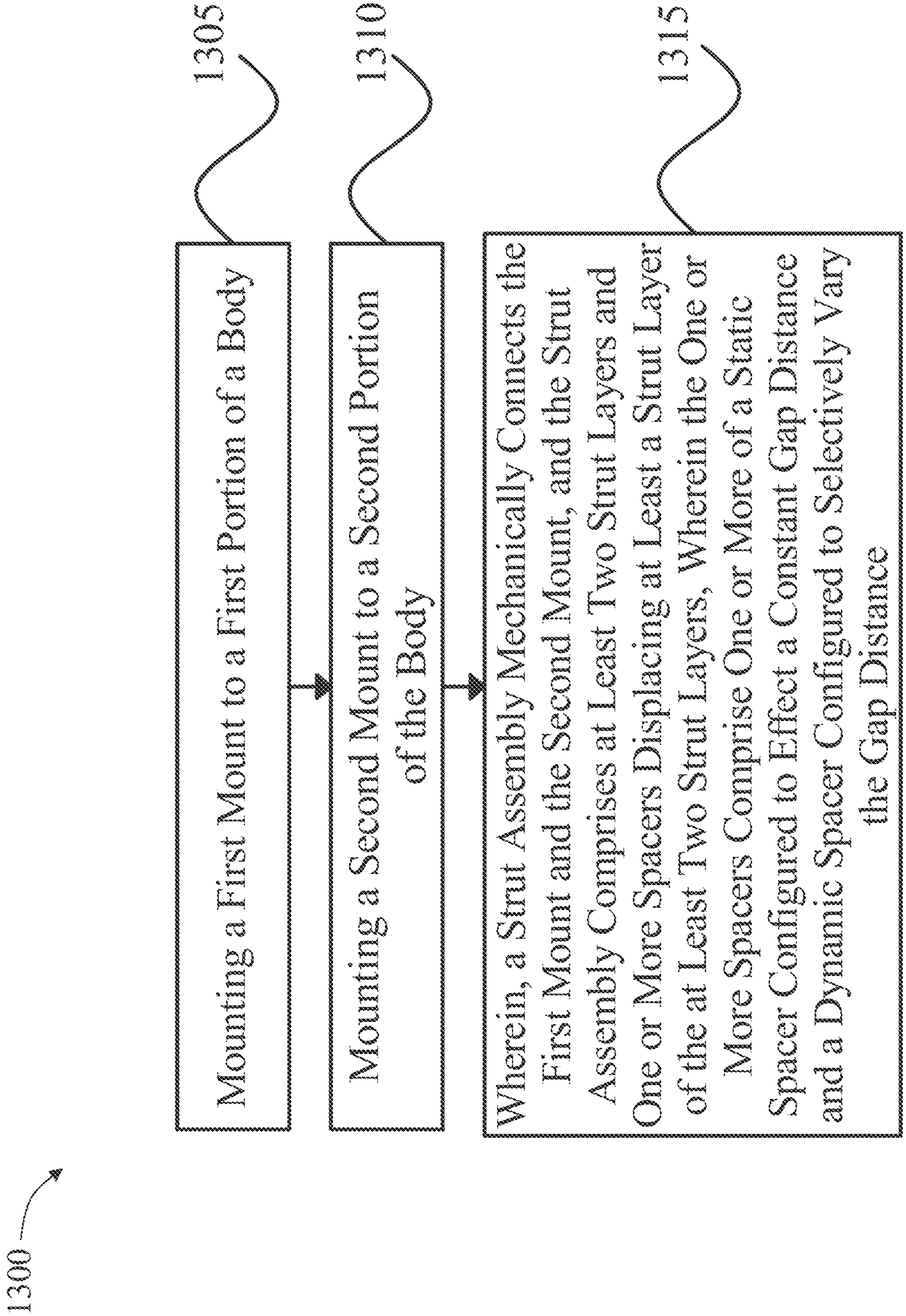
FIG. 13 is a flow diagram of an exemplary method for use of an adaptive stiffness energy return structure for orthopedics.

Now referring to FIG. 13, an exemplary method 1300 for using an adaptive energy return structure for orthopedics is illustrated. Method 1300 may include a step 1305 of engaging a first mount with a user. This may be implemented, without limitation, as referenced in FIGS. 1-12. Method 1300 may include a step 1310 of positioning a second mount to at least partially surround a portion of a body. This may be implemented, without limitation, as referenced in FIGS. 1-12.

Method 1300 may include a step 1315 of adjusting the spacing between at least two strut layers of a strut assembly mechanically connected to the first mount, wherein the gap between the at least two strut layers is affected by one or more spacers that display at least one of the strut layers, wherein the one or more spacers include at least one static spacer to maintain a constant gap distance and at least one dynamic spacer to vary the gap distance. In an embodiment, the displacement of the at least a strut layer caused by the one or more spacers may vary a load on the structure, such that the load is increased or decreased as a function of the gap distance between the at least two strut layers. In an embodiment, the strut assembly may include a proximal and distal end and each of the proximal and distal ends of the at least two strut layers may be mechanically connected by one or more connecting assemblies, wherein the one or more connecting assemblies include one or more bushings and one or more mounting plates attached to the one or more bushings. Further, in some embodiments, the strut assembly may include a proximal end, a center, a distal end, and a spreading strut assembly. The spreading strut assembly may include one or more static spacers located between the at least two strut layers at both the proximal and distal end of the strut assembly, a dynamic spacer located near the center of the strut assembly and configured to spread the at least two strut layers apart when acted on in a first direction and bring the at least two strut layer together when acted on in a second direction, and one or more grips, wherein the one or more grips are affixed to the dynamic spacer. In an embodiment, the dynamic spacer may include an actuator configured to adjust a dynamic spacer of the one or more dynamic spacers to set a gap between the at least two strut layers. In an embodiment, the structure may further include one or more straps attached to a distal and proximal end of the structure, a linear actuator communicatively connected to the one or more straps, wherein ta linear actuator is configure to adjust the one or more straps, thereby controlling the space between the distal and proximal ends of the strut assembly, and wherein the linear actuator include a handle configured to increase and decrease a stiffness fo the at least two strut layers. This may be implemented, without limitation, as referenced in FIGS. 1-12.

In continued reference to FIG. 13, in one or more embodiments, method 1300 may further include detecting pressure data using a pressure sensor system, wherein detecting pressure data includes detecting a pressure datum, and adjusting a distance between the at least two strut layers using the actuator as a function of the pressure datum. Further, in some embodiments, the actuator may include a threaded rod configured to adjust a distance between the at least two strut layers. In some cases the actuator may include an electronic controller, wherein the electronic controller is configured to receive one or more electronic control signals, wherein the electronic control signals represent pressure, strain, and/or movement, and adjust the spacing between the at least two strut layers as a function of the one or more electronic control signals. This may be implemented, without limitation, as referenced in FIGS. 1-12.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 14:
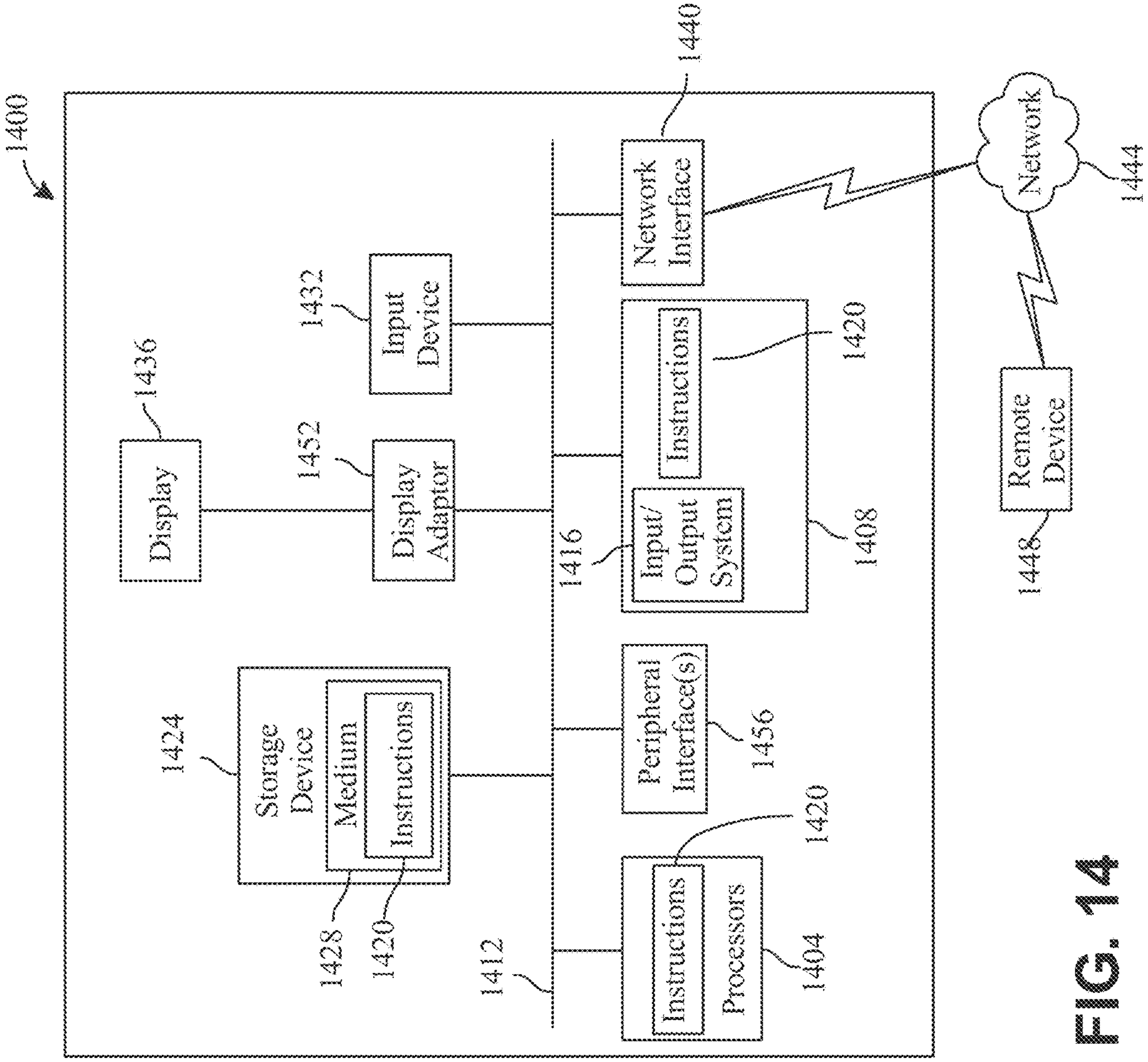
FIG. 14 is a block diagram of a computing system that can be used to implement any one or more of the methodologies disclosed herein and any one or more portions thereof.

FIG. 14 shows a diagrammatic representation of one embodiment of a computing device in the exemplary form of a computer system 1400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1400 includes a processor 1404 and a memory 1408 that communicate with each other, and with other components, via a bus 1412. Bus 1412 may include any of several types of bus structures including, but not limited to, a memory bus, a memory controller, a peripheral bus, a local bus, and any combinations thereof, using any of a variety of bus architectures.

Processor 1404 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1404 may be organized according to Von Neumann and/or Harvard architecture as a non-limiting example. Processor 1404 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1408 may include various components (e.g., machine-readable media) including, but not limited to, a random-access memory component, a read only component, and any combinations thereof. In one example, a basic input/output system 1416 (BIOS), including basic routines that help to transfer information between elements within computer system 1400, such as during start-up, may be stored in memory 1408. Memory 1408 may also include (e.g., stored on one or more machine-readable media) instructions (e.g., software) 1420 embodying any one or more of the aspects and/or methodologies of the present disclosure. In another example, memory 1408 may further include any number of program modules including, but not limited to, an operating system, one or more application programs, other program modules, program data, and any combinations thereof.

Computer system 1400 may also include a storage device 1424. Examples of a storage device (e.g., storage device 1424) include, but are not limited to, a hard disk drive, a magnetic disk drive, an optical disc drive in combination with an optical medium, a solid-state memory device, and any combinations thereof. Storage device 1424 may be connected to bus 1412 by an appropriate interface (not shown). Example interfaces include, but are not limited to, SCSI, advanced technology attachment (ATA), serial ATA, universal serial bus (USB), IEEE 1494 (FIREWIRE), and any combinations thereof. In one example, storage device 1424 (or one or more components thereof) may be removably interfaced with computer system 1400 (e.g., via an external port connector (not shown)). Particularly, storage device 1424 and an associated machine-readable medium 1428 may provide nonvolatile and/or volatile storage of machine-readable instructions, data structures, program modules, and/or other data for computer system 1400. In one example, software 1420 may reside, completely or partially, within machine-readable medium 1428. In another example, software 1420 may reside, completely or partially, within processor 1404.

Computer system 1400 may also include an input device 1432. In one example, a user of computer system 1400 may enter commands and/or other information into computer system 1400 via input device 1432. Examples of an input device 1432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1432 may be interfaced to bus 1412 via any of a variety of interfaces (not shown) including, but not limited to, a serial interface, a parallel interface, a game port, a USB interface, a FIREWIRE interface, a direct interface to bus 1412, and any combinations thereof. Input device 1432 may include a touch screen interface that may be a part of or separate from display 1436, discussed further below. Input device 1432 may be utilized as a user selection device for selecting one or more graphical representations in a graphical interface as described above.

A user may also input commands and/or other information to computer system 1400 via storage device 1424 (e.g., a removable disk drive, a flash drive, etc.) and/or network interface device 1440. A network interface device, such as network interface device 1440, may be utilized for connecting computer system 1400 to one or more of a variety of networks, such as network 1444, and one or more remote devices 1448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1444, may employ a wired and/or a wireless mode of communication. In general, any network topology may be used. Information (e.g., data, software 1420, etc.) may be communicated to and/or from computer system 1400 via network interface device 1440.

Computer system 1400 may further include a video display adapter 1452 for communicating a displayable image to a display device, such as display device 1436. Examples of a display device include, but are not limited to, a liquid crystal display (LCD), a cathode ray tube (CRT), a plasma display, a light emitting diode (LED) display, and any combinations thereof. Display adapter 1452 and display device 1436 may be utilized in combination with processor 1404 to provide graphical representations of aspects of the present disclosure. In addition to a display device, computer system 1400 may include one or more other peripheral output devices including, but not limited to, an audio speaker, a printer, and any combinations thereof. Such peripheral output devices may be connected to bus 1412 via a peripheral interface 1456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An adaptive stiffness energy return structure, wherein the structure comprises:

a first mount configured to mount with a first portion of a user's body;

a second mount configured to mount to a second portion of the user's body; and a strut assembly with continuously variable stiffness, mechanically connecting the first mount and the second mount, wherein the strut assembly comprises:

at least two strut layers; and two or more spacers displacing at least a strut layer of the at least two strut layers and affecting a gap between the at least two strut layers, wherein the two or more spacers comprise one or more of a static spacer configured to affect a constant gap distance and one or more of a dynamic spacer configured to selectively vary the gap distance, wherein the dynamic spacer comprises a threaded rod configured to adjust the gap distance between the at least two strut layers, wherein the threaded rod comprises right-hand and left-hand thread segments respectively engaged through threaded inserts to the at least two strut layers, such that rotation in a first direction increases the gap distance and rotation in a second direction decreases the gap distance.

2. The structure of claim 1, wherein the displacement of the at least a strut layer caused by the two or more spacers imparts a load on the structure as a function of the gap distance between the at least two strut layers.

3. The structure of claim 1, wherein:

the strut assembly comprises a proximal and a distal end; and each of the proximal and distal ends of the at least two strut layers is mechanically connected, by one or more connecting assemblies, to either the first mount or the second mount, wherein the one or more connecting assemblies comprise:

one or more bushings; and one or more mounting plates attached to the one or more bushings.

4. The structure of claim 1, wherein the strut assembly further comprises a proximal end;

a center;

a distal end; and a spreading strut assembly, comprising:

the dynamic spacer located near the center of the strut assembly and configured to selectively vary the gap distance proportionally to user input; and one or more grips, wherein the one or more grips are affixed to the dynamic spacer configured to receive user input.

5. The structure of claim 1, wherein the two or more spacers comprise a bladder configured to inflate and deflate in response to an external stimulus, thereby adjusting the gap between the at least two strut layers.

6. The structure of claim 1, wherein another one of the one or more dynamic spacers comprises one or more of: shims, wedges, cams, bladders, bushings, and washers.

7. The structure of claim 1, wherein the dynamic spacer comprises an actuator configured to adjust the dynamic spacer to selectively vary the gap distance between the at least two strut layers.

8. The structure of claim 7, wherein the actuator comprises one or more of: a linear actuator, a rotary actuator, an electro-magnetic actuator, a pneumatic actuator, and a hydraulic actuator.

9. The structure of claim 7, wherein the structure further comprises:

a pressure sensor system, wherein the pressure sensor system is configured to:

detect a pressure datum; and an electronic controller, wherein the electronic controller is configured to:

receive one or more electronic control signals from a pressure sensor; and adjust the gap distance between the at least two strut layers as a function of the one or more electronic control signals.

10. A method of using an adaptive stiffness energy return structure, the method comprising:

mounting a first mount to a first portion of a body;

mounting a second mount to a second portion of the body; wherein:

a strut assembly with continuously variable stiffness mechanically connects the first mount and the second mount; and the strut assembly comprises:

at least two strut layers; and two or more spacers displacing at least a strut layer of the at least two strut layers and affecting a gap between the at least two strut layers, wherein the two or more spacers comprise one or more of a static spacer configured to affect a constant gap distance and one or more of a dynamic spacer configured to selectively vary the gap distance, wherein the dynamic spacer comprises a threaded rod configured to adjust the gap distance between the at least two strut layers, wherein the threaded rod comprises right-hand and left-hand thread segments respectively engaged through threaded inserts to the at least two strut layers, such that rotation in a first direction increases the gap distance and rotation in a second direction decreases the gap distance.

11. The method of claim 10, further comprising imparting a load, using the two or more spacers, on the structure as a function of the gap distance between the at least two strut layers.

12. The method of claim 10, wherein:

the strut assembly comprises a proximal and a distal end; and each of the proximal and distal ends of the at least two strut layers is mechanically connected, by one or more connecting assemblies, to either the first mount or the second mount, wherein the one or more connecting assemblies comprise:

one or more bushings; and one or more mounting plates attached to the one or more bushings.

13. The method of claim 10, wherein the strut assembly further comprises a proximal end;

a center;

a distal end; and a spreading strut assembly, and the method further comprises:

selectively varying, using the dynamic spacer located near the center of the strut assembly, the gap distance proportionally to user input; and receiving, using one or more grips affixed to the dynamic spacer the user input.

14. The method of claim 10, wherein the two or more spacers comprise a bladder and the method further comprises:

inflating and deflating, in response to an external stimulus, the bladder to adjust the gap between the at least two strut layers.

15. The method of claim 10, wherein the another one of the one or more dynamic spacers comprises one or more of: shims, wedges, cams, bladders, bushings, and washers.

16. The method of claim 10, wherein the dynamic spacer comprises an actuator and the method comprises adjusting, using the actuator, the dynamic spacer to selectively vary the gap distance between the at least two strut layers.

17. The method of claim 16, wherein the actuator comprises one or more of: a linear actuator, a rotary actuator, an electro-magnetic actuator, a pneumatic actuator, and a hydraulic actuator.

18. The method of claim 16, wherein the method further comprises:

detecting, using a pressure sensor system, a pressure datum;

receiving, using an electronic controller, one or more electronic control signals representing the pressure datum from a pressure sensor; and adjusting, using the electronic controller and the actuator, the gap distance between the at least two strut layers as a function of the one or more electronic control signals.

* * * * *